(12) United States Patent
Grgurevic et al.

(10) Patent No.: US 8,263,072 B2
(45) Date of Patent: Sep. 11, 2012

(54) ADAMTS4 AS A BLOOD BIOMARKER AND THERAPEUTIC TARGET FOR CHRONIC RENAL FAILURE

(75) Inventors: Lovorka Grgurevic, Zagreb (HR); Slobodan Vukicevic, Zagreb (HR)

(73) Assignee: Genera Istrazivanja, d.o.o., Kalinovica (HR)

( * ) Notice: Subject to any disclaimer, the term of this patent is extended or adjusted under 35 U.S.C. 154(b) by 0 days.

(21) Appl. No.: 12/665,270

(22) PCT Filed: Jun. 20, 2008

(86) PCT No.: PCT/US2008/007713
§ 371 (c)(1),
(2), (4) Date: Dec. 17, 2009

(87) PCT Pub. No.: WO2009/002451
PCT Pub. Date: Dec. 31, 2008

(65) Prior Publication Data
US 2010/0254997 A1    Oct. 7, 2010

Related U.S. Application Data

(60) Provisional application No. 60/936,850, filed on Jun. 22, 2007.

(51) Int. Cl.
*A61K 39/395*      (2006.01)
(52) U.S. Cl. .................................. 424/130.1; 424/139.1
(58) Field of Classification Search .................... None
See application file for complete search history.

(56) References Cited

U.S. PATENT DOCUMENTS

| | | | |
|---|---|---|---|
| 5,693,762 | A | 12/1997 | Queen et al. |
| 6,734,007 | B2 | 5/2004 | Friddle et al. |
| 7,850,964 | B2 | 12/2010 | Vukicevic et al. |
| 2002/0090373 | A1 | 7/2002 | Buckbinder et al. |
| 2003/0129658 | A1 | 7/2003 | Yamaji et al. |
| 2004/0142863 | A1 | 7/2004 | Corcoran et al. |
| 2006/0228354 | A1* | 10/2006 | Corcoran et al. .......... 424/143.1 |

FOREIGN PATENT DOCUMENTS

| | | |
|---|---|---|
| EP | 0 239 400 B1 | 8/1994 |
| EP | 0 875 571 A2 | 11/1998 |
| EP | 1 508 619 A1 | 2/2005 |
| WO | WO 90/05144 A1 | 5/1990 |
| WO | WO 00/53774 A2 | 9/2000 |
| WO | WO 2007/134718 A2 | 11/2007 |

OTHER PUBLICATIONS

Totorella et al., "α2-Macroglobulin is a novel substrate for ADAMTS-4 and ADAMTS-5 and represents an endogenous inhibitor of these enzymes," J. Biol. Chem., 279: 17554-17461 (2004).
Abbaszade et al., "Cloning and Characterization of ADAMTS11, an Aggrecanase from the ADAMTS Family", J. Biol. Chem., 274(33): 23443-23450 (1999).
Bird et al., "Single-Chain Antigen-Binding Proteins", Science, 242: 423-426 (1988).
Borovecki et al., In Bone Morphogenetic Proteins: From Laboratory to Clinical Practice, (Vukicevic and Sampath, eds.) (Birkhauser Verlag, Basel), pp. 263-288 (2002).
Borovecki et al., "The role of bone morphogenetic proteins in developing and adult kidney", In Bone Morphogenetic Proteins: Regeneration of bone and beyond, (Vukicevic and Sampath, eds.) (Birkhauser Verlag, Basel), pp. 213-243 (2004).
Gao et al., "Activation of the Proteolytic Activity of ADAMTS4 (Aggrecanase-1) by C-terminal Truncation", J. Biol. Chem., 277(13): 11034-11041 (2002).
Gendron et al., "Proteolytic Activities of Human ADAMTS-5, Comparative Studies with ADAMTS-4", J. Biol. Chem., 282: 18294-18306 (2007).
Glasson et al., "Characterization of and Osteoarthritis Susceptibility in ADAMTS-4-Knockout Mice", Arthritis Rheum., 50(8): 2547-2558 (2004).
Glasson et al., "Deletion of active ADAMTS5 prevents cartilage degradation in murine model of osteoarthritis", Nature, 434: 644-648 (2005).
Hashimoto et al., "ADAMTS4 (Aggrecanase-1) Interaction with the C-terminal Domain of Fibronectin Inhibits Proteolysis of the Aggrecan", J. Biol. Chem., 279(31): 32483-32491 (2004).
Holliger et al., "Diabodies": Small bivalent and bispecific antibody fragments, Proc. Natl. Acad. Sci. USA, 90: 6444-6448 (1993).
Holliger et al., "Diabodies: small bispecific antibody fragements", Cancer Immunol. Immunother., 45: 128-130 (1997).
Huston et al., "Protein engineering of antibody binding sites: Recovery of specific activity in an anti-digoxin single-chain Fv analogue produced in *Escherichia coli*", Proc. Natl. Acad. Sci. USA, 85: 5879-5883 (1988).
Kriangkum et al., "Bispecific and bifunctional single chain recombinant antibodies", Biomol. Eng., 18: 31-40 (2001).
Kuno et al., "Molecular Cloning of a Gene Encoding a New Type of Metalloproteinase-disintegrin Family Protein with Thrombospondin Motifs as an Inflammation Associated Gene", J. Biol. Chem., 272(1): 556-562 (1997).
Kveiborg et al., "A Role for ADAM12 in Breast Tumor Progression and Stromal Cell Apoptosis", Cancer Res., 65(11): 4754-4761 (2005).
Llamazares et al., "Identification and Characterization of ADAMTS-20 Defines a Novel Subfamily of Metalloproteinases-Disintegrins with Mulitple Thrombospondin-1 Repeats and a Unique GON Domain", J. Biol. Chem., 278(15): 13382-13389 (2003).
Miller et al., "Design, Construction, and In Vitro Analyses of Multivalent Antibodies", J. Immunol., 170: 4854-4861 (2003).
Milstein et al., "Hybrid hybridomas and their use in immunohistochemistry", Nature, 305: 537-540 (1983).
Mochizuki et al., "ADAMs in cancer cell proliferation and progression", Cancer Sci., 98(5): 621-628 (2007).
Naito et al., "Expression of ADAMTS4 (aggrecanase-1) in human osteoarthritic cartilage", Pathol. Int., 57: 703-711 (2007).
Poljak, R.J., "Production and structure of diabodies", Structure, 2: 1121-1123 (1994).

(Continued)

*Primary Examiner* — Marianne P Allen
(74) *Attorney, Agent, or Firm* — Thomas R. Berka; Leon R. Yankwich; Yankwich & Associates, P.C.

(57) ABSTRACT

ADAMTS4 is found to be useful as a blood biomarker for chronic renal failure and also as a therapeutic target for treating chronic renal failure in a human individual. A change in the level of expression of selected genes as disclosed herein in kidney tissue of an individual may also be used to diagnose chronic renal failure in an individual.

4 Claims, 7 Drawing Sheets

OTHER PUBLICATIONS

Porter et al., "The ADAMTS metalloproteinases" Biochem. J., 386: 15-27 (2005).

Queen et al., "A humanized antibody that binds to the interleukin 2 receptor", Proc. Natl. Acad. Sci. USA, 86: 10029-10033 (1989).

Richards et al., "Regulated Expression of ADAMTS Family Members in Follicles and Cumulus Oocyte Complexes: Evidence for Specific and Redundant Patterns During Ovulation", Biol. Reproduct., 72: 1241-1255 (2005).

Song et al., "Aggrecan Degradation in Human Articular Cartilage Explants Is Mediated by Both ADAMTS-4 and ADAMTS-5", Arthritis Rheum., 56(2): 575-585 (2007).

Tortorella et al., "Purification and Cloning of Aggrecanase-1: A Member of the ADAMTS Family of Proteins", Science, 284: 1664-1666 (1999).

Tortorella et al., "The role of ADAM-TS4 (aggrecanase-1) and ADAM-TS5 (aggrecanase-2) in a model of cartilage degradation", Osteoarthritis and Cartilage, 9: 539-552 (2001).

Vukicevic et al., "Osteogenic Protein-1 (Bone Morphogenetic Protein-7) Reduces Severity of Injury After Ischemic Acute Renal Failure in Rat", J. Clin. Invest., 102(1): 202-214 (1998).

Wang et al., "Proprotein Convertase Furin Interacts with and Cleaves Pro-ADAMTS4 (Aggrecanase-1) in the trans-Golgi Network", J. Biol. Chem., 279: 15434-15440 (2004).

Ward et al., "Binding activities of a repertoire of single immunoglobulin variable domains secreted from *Escherichia coli*", Nature, 341: 544-546 (1989).

Wu et al., "Simultaneous targeting of multiple disease mediators by a dual-variable-domain immunoglobulin", Nature Biotechnology (Advance Online Publication), 2007 Nature Publishing Group, 1-8 http://www.nature.com/naturebiotechnology.

Yamanishi et al., "Expression and Regulation of Aggrecanase in Arthritis: The Role of TGF-β", J. Immunol., 168: 1405-1412 (2002).

Anti-ADAMTS4 antibody—Carboxyterminal end (ab28285), [Data sheet, 2 pgs.]. Retrieved Oct. 28, 2011, from http://www.abcam.com/ADAMTS4-antibody-Carboxyterminal-end-ab28285.html.

ADAMTS4 peptide (Carboxyterminal end) (ab41235), [Data sheet, 1 pg.]. Retrieved Oct. 28, 2011, from http://www.abcam.com/ADAMTS4-peptide-Carboxyterminal-end-ab41235.html.

Chow et al., "Animal Remnant Kidney Model of Chronic Renal Failure Revisited," Hong Kong J. Nephrol., 5(2): 57-64 (2003).

Dai et al., "Animal Models of Kidney Diseases," chapter 68, In Sourcebook of Models for Biomedical Research (P. M. Conn, ed.) (Humana Press Inc., Totowa, New Jersey, 2008) pp. 657-664.

National Kidney Foundation, Inc. (NKF) K/DOQI, Guidelines 1 and 2, American Journal of Kidney Diseases, 39(2) Suppl. 1 (February): S46-S75 (2002).

Vukicevic et al., "Role of EP2 and EP4 receptor-selective agonists of prostaglandin E2 in acute and chronic kidney failure," Kidney Int., 70: 1099-1106 (2006).

* cited by examiner

ABSTRACT

ADAMTS4 AS A BLOOD BIOMARKER AND THERAPEUTIC TARGET FOR CHRONIC RENAL FAILURE

CROSS-REFERENCE TO RELATED APPLICATIONS

This application is a U.S. national stage filing under 35 USC §371 of international application No. PCT/US2008/007713, filed Jun. 20, 2008, designating the U.S., which claims priority to U.S. Provisional Application No. 60/936,850, filed Jun. 22, 2007.

BACKGROUND OF THE INVENTION

Chronic renal failure (CRF), or the more recently coined term "chronic kidney disease" (CKD), is a progressive deterioration and loss of renal function typically over a relatively long time period such as months to years. There are five recognized stages of CRF (CKD) based primarily on glomerular filtration rate (GFR). Although a GFR of greater than 90 mL/min/1.73 m$^2$ ("90 mL/min") is considered normal, an individual with a GFR greater than 90 ml/min may nonetheless be classified as stage 1 CRF if he/she has experienced some form of kidney damage as evidenced by abnormal blood or urine markers of kidney damage (e.g., increased creatinine levels), abnormal imaging results, and/or has one or more risk factors (e.g., proteinuria, diabetes, high blood pressure, family history of CRF, cardiovascular disease). Stage 2 CRF (CKD) is characterized by a relatively mild reduction in GFR to 60-89 mL/min/1.73 m$^2$ ("60-89 mL/min") along with any of the other risk factors of stage 1, stage 3 by a GFR of 30-59 mL/min, stage 4 by a GFR of 15-29 mL/min, and stage 5 by a GFR of less than 15 mL/min. Stage 5 CRF is also referred to as end-stage renal disease (ESRD), and such patients will not survive long, particularly as the GFR approaches 5-10 ml/min, without some form of renal replacement therapy, such as dialysis or kidney transplantation.

Currently, there is no approved therapy to reverse the progression of CRF from stage 1 to stage 5 (ESRD), although early diagnosis along with current therapy may delay progression to ESRD and the need for renal replacement therapy. Both dialysis and kidney transplantation can present a variety of risks or side effects to the patient, such as infection, rejection of organ transplant, and fatigue with treatment, which can ultimately lead to patient mortality.

In the United States, billions of dollars are currently necessary to provide renal replacement therapy, and such costs are expected to increase. Accordingly, delaying the need to provide renal replacement therapy, including lengthening the time between dialysis treatments of currently diagnosed ESRD patients, would both provide a significant benefit to a CRF patient's quality of life and also significantly lower costs of treatment by decreasing the number of dialysis sessions and decreasing overall the number of kidney transplants that need to be performed.

In the current circumstances, there is a clear need for improved methods for diagnosis and treatment of chronic renal failure.

SUMMARY OF THE INVENTION

The present invention is based on the discovery that the protein ADAMTS4 (a disintegrin and metalloproteinase with thrombospondin type 1 motif-4, aggrecanase-1) appears in the peripheral (venous) blood of human patients with end-stage chronic renal failure (stage 5, end-stage renal disease (ESRD)). ADAMTS4 is not present in the blood of normal healthy human individuals. Stage 5 CRF patients have a glomerular filtration rate (GFR) that is typically less than 10% of normal values (e.g., less than 15 mL/min/1.73 m$^2$) and will not survive without some form of renal replacement therapy such as kidney transplantation or dialysis. Dialysis can temporarily clear ADAMTS4 from the peripheral circulation of a CRF patient, but like other toxins and wastes, the ADAMTS4 metalloproteinase then reappears and accumulates in the blood as the dialysis patient's condition deteriorates and time approaches for another dialysis treatment. As shown herein, ADAMTS4 is a uremic toxin that is useful as a blood biomarker for CRF and as a target for treating individuals with CRF.

In one embodiment, the invention provides a method of detecting chronic renal failure (CRF) in a human individual comprising the steps of assaying a sample of blood obtained from the individual for the presence of ADAMTS4, wherein detection of the presence of ADAMTS4 in the blood sample indicates that the individual has CRF.

Methods of detecting ADAMTS4 in a sample of blood obtained from an individual may also be used to measure (quantitate) the level of ADAMTS4 present in the sample of blood and thereby in the blood of the individual.

Methods of detecting or quantitating ADAMTS4 as described herein may be carried out on whole blood or a fraction thereof, such as plasma or serum. Preferably, the plasma portion of blood is used in methods described herein.

In another embodiment, the invention provides a method of monitoring uremic toxicity of a human individual (patient) with chronic renal failure (CRF) between dialysis treatments comprising obtaining a first blood sample from the patient at a first time point after a dialysis treatment, obtaining at least one additional blood sample from said individual at a later time point after the dialysis treatment, determining the level (amount, concentration) of ADAMTS4 in said first blood sample and in said at least one additional blood sample, wherein an increase in ADAMTS4 concentration between said first blood sample and said at least one additional sample indicates that the individual has an increasing uremic toxicity, which may indicate the need for therapeutic intervention (e.g., scheduling a dialysis session or kidney transplant). Conversely, steady levels of ADAMTS4, decreasing levels, or only insignificantly increased levels may indicate that further therapeutic intervention may be delayed or postponed. In a preferred embodiment said first time point (first sample) and said later time point(s) (additional sample(s)) are within two weeks of each other. More preferably, said first time point and said later time point are within one week, even more preferably within three days, and even more preferably within two days, of each other.

Preferably, in a method described herein, a blood sample is assayed for the presence or amount of ADAMTS4 using a binding partner that specifically binds ADAMTS4 as its cognate binding partner (cognate ligand). Binding partners include binding proteins and aptamers. Preferably a binding partner is a binding protein, and more preferably an antibody recognizing ADAMTS4. Antibody molecules useful in the methods and compositions described herein include, but are not limited to, full-length immunoglobulin antibody molecules comprising four polypeptide chains, i.e., two heavy (H) chains and two light (L) chains, wherein each pair of heavy and light chains forms a binding site for ADAMTS4 or an epitope thereof. An antibody molecule useful in the methods and compositions described herein may be a polyclonal antibody or a monoclonal antibody. Other antibody molecules useful in the methods and compositions described herein include any of a variety of recombinant antibody molecules that possess a binding site for the ADAMTS4 antigen or epitope thereof, including without limitation, a functional antibody fragment, such a Fab, F(ab')$_2$, and Fv; a hybrid antibody, such as a chimeric or humanized antibody; a single chain antibody (scFv); a diabody; a dual-variable domain immunoglobulin molecule; and the like. Antibody binding proteins for ADAMTS4 are especially advantageous as they may be employed in any of a variety of immunoassay formats in which a blood sample of an individual is brought into contact with an antibody binding protein for ADAMTS4 under conditions suitable for the formation of a binding complex formed between the antibody binding protein and its cognate ADAMTS4-binding partner, which complex can then be detected using any of a variety of methods available in the art for detecting antibody/antigen immunocomplexes.

A binding partner, such as an ADAMTS4 antibody, used in methods and compositions described herein to detect or quantitate ADAMTS4 in a sample of blood may have an attached detectable label (tag) that generates a detectable or quantifiable signal when the binding partner is bound to ADAMTS4 in a binding complex. In an alternative approach, a first antibody may be used to bind to ADAMTS4 in a blood sample to form a binding complex, and a second antibody that has a detectable label may be used to bind to the first antibody or to the ADAMTS4 in the binding complex. Detectable labels and other molecules that can be attached to antibodies and other molecules are well known in the art and include, without limitation, light generating molecules, fluorescent labels, radiolabels, colorimetric molecules, and affinity beads.

Formats used for immunoassays to detect antibody/antigen immunocomplexes may also be employed in the methods and compositions described herein. Such formats for detecting or measuring the level of ADAMTS4 in a sample of blood according to the invention include, but are not limited to, enzyme-linked immunosorbent assay (ELISA), immunoprecipitations, immunoblotting, affinity chromatography, assay strips, dip sticks, and the like, wherein the blood sample is brought into contact with an antibody for ADAMTS4 and the resulting binding complex detected.

In yet another embodiment, the invention provides a kit for detecting or measuring the level of ADAMTS4 in a sample of blood from an individual to determine if the individual has chronic renal failure. Such kits may comprise a binding partner for ADAMTS4, such as an ADAMTS4 antibody, one or more buffers or solutions for carrying out the assay, and instructions that indicate how to use the kit to detect the presence of or measure the level of ADAMTS4 in a blood sample.

In another embodiment, the invention provides a method of treating a human individual for chronic renal failure comprising the step of administering to the individual an ADAMTS4-binding protein such as an antibody to ADAMTS4.

In yet another embodiment, the invention provides a method of increasing the time between dialysis treatments for a human individual with CRF comprising administering to the individual an ADAMTS4-binding protein, such as an ADAMTS4 antibody, in an amount effective to reduce or clear the presence of ADAMTS4 from the blood of the individual or to inhibit its proteinase activity in the individual.

In methods described herein for treating an individual with CRF, an ADAMTS4-binding protein may be administered to the individual parenterally or non-parenterally. More preferably, an ADAMTS4-binding protein is administered to an individual parenterally, and even more preferably, intravenously.

As shown herein, the presence of ADAMTS4 in the blood of an individual is indicative of chronic renal failure and is also correlated with a change in the expression of certain genes in the kidney tissue of the individual. In particular, ADAMTS4 in the blood is correlated with an increase in kidney tissue in the level of expression of genes for proteoglycan-4 (lubricin) and aggrecan and with a decrease in the level of expression of genes for TSP-1, BMP-1, and BMP-7. The level of expression of these genes can be readily determined using kidney tissue obtained from an individual by routine renal biopsy. Accordingly, in another embodiment, the invention provides a method of detecting chronic renal failure (CRF) in an individual comprising obtaining a first sample of kidney tissue from the individual at a first time point, obtaining at least one additional sample of kidney tissue from said individual at a later time point, determining the level of expression of genes for one or more of the proteins from the group proteoglycan-4, aggrecan, TSP-1, BMP-1, and BMP-7 in said first kidney tissue sample and in said at least one additional kidney tissue sample, wherein an increase in the level of expression of the genes for proteoglycan-4 and/or aggrecan and a decrease in the level of expression of the genes for TSP-1, BMP-1, and/or BMP-7 between said first time point and said later time point indicates that the individual has chronic renal failure. In a preferred embodiment said first time point and said later time point(s) are within two weeks of each other. More preferably, samples are taken less than a week apart, more preferably samples are taken less than three day apart; most preferably samples are taken less than two days apart.

Bar graph 3 shows the fold change in gene expression in kidney tissue from SNX rats treated with 2 μg the ADAMTS4 polypeptide relative to control. Asterisk indicates statistically significant decrease relative to controls (P<0.05). Bar graph 4 shows the fold change in gene expression in kidney tissue from SNX rats treated with antibody to ADAMTS4 relative to control. See Example 4, for details.

Figure 4:
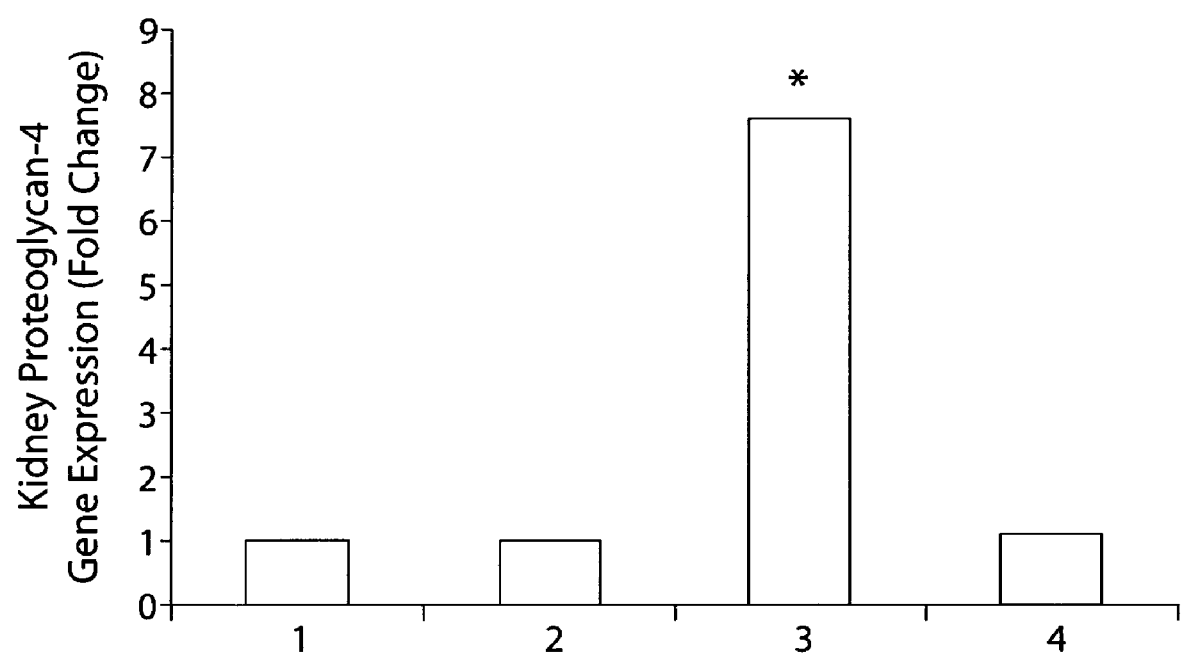

FIG. 4 shows the fold change in the level of expression of the proteoglycan-4 (lubricin) gene in kidney tissue obtained from subtotally (5/6) nephrectomized (SNX) rats in control and various treatments groups relative to the level of expression in kidney tissue from the control group in the study described in Example 4 (infra). Bar graph 1 shows a fold change of 1 (relative to self) in proteoglycan-4 gene expression in kidney tissue from untreated control SNX rats that received vehicle (HEPES buffer) only. Bar graph 2 shows the fold change in gene expression in kidney tissue from SNX rats treated with 0.5 μg of active ADAMTS4 carboxy terminal polypeptide relative to control. Bar graph 3 shows the fold change in gene expression in kidney tissue from SNX rats treated with 2 μg the ADAMTS4 polypeptide relative to control. Asterisk indicates statistically significant increase relative to controls (P<0.05). Bar graph 4 shows the fold change in gene expression in kidney tissue from SNX rats treated with antibody to ADAMTS4 relative to control. See Example 4, for details.

Figure 5:
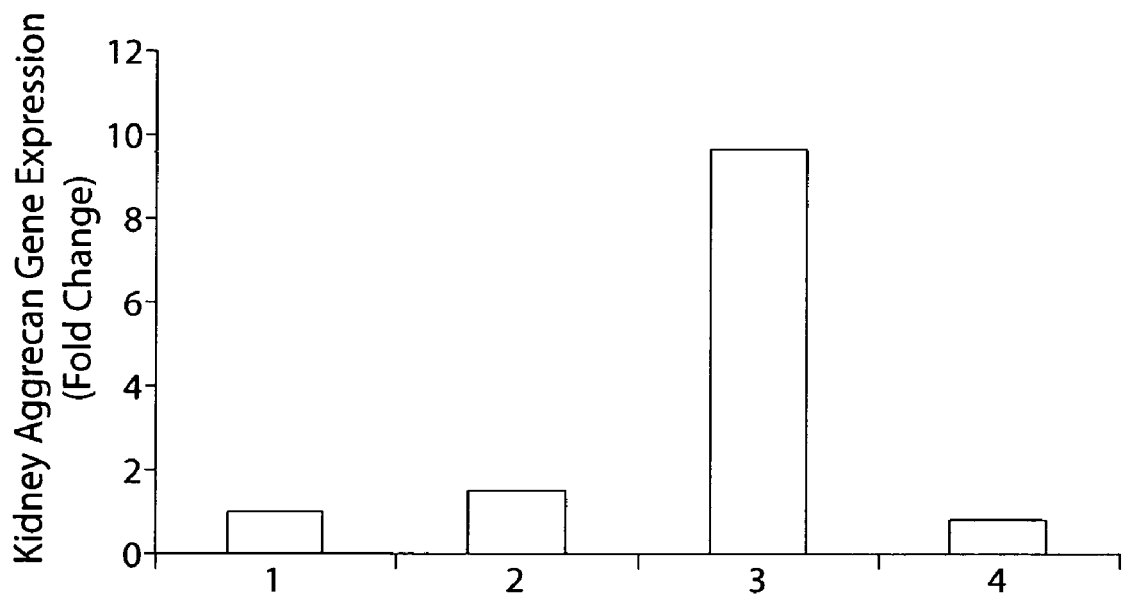

FIG. 5 shows the fold change in the level of expression of the aggrecan gene in kidney tissue obtained from subtotally (5/6) nephrectomized (SNX) rats in control and various treatment groups relative to the level of expression in kidney tissue from the control group in the study described in Example 4 (infra). Bar graph 1 shows a fold change of 1 (relative to self) in aggrecan gene expression in kidney tissue from untreated control SNX rats that received vehicle (HEPES buffer) only. Bar graph 2 shows the fold change in gene expression in kidney tissue from SNX rats treated with 0.5 μg of active ADAMTS4 carboxy terminal polypeptide relative to control. Bar graph 3 shows the fold change in gene expression in kidney tissue from SNX rats treated with 2 μg of the ADAMTS4 polypeptide relative to control. Bar graph 4 shows the fold change in gene expression in kidney tissue from SNX rats treated with antibody to ADAMTS4 relative to control. See Example 4, for details.

Figure 6:
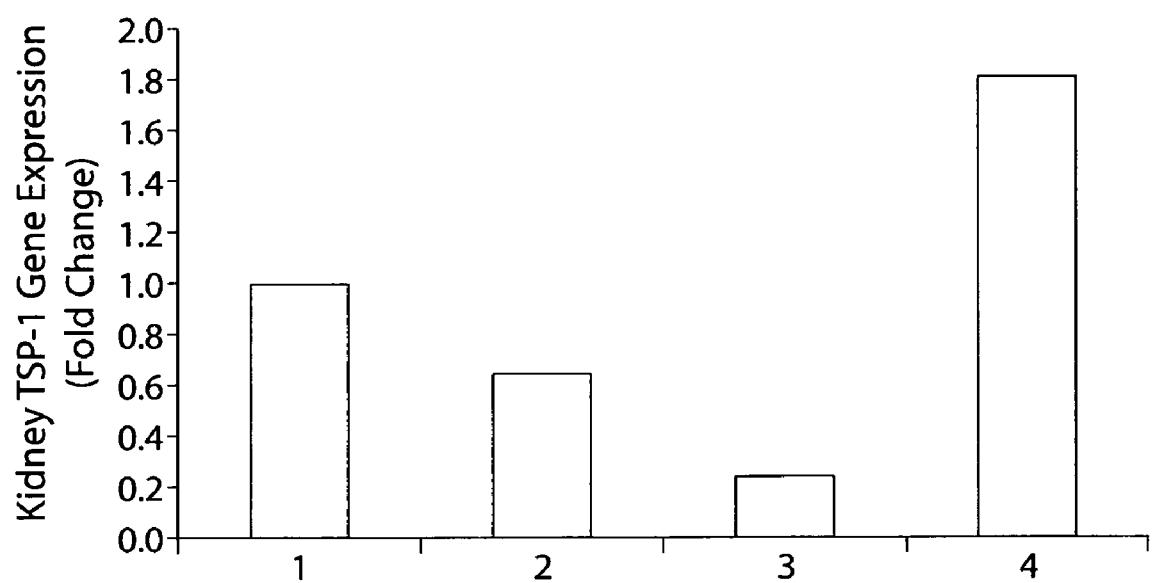

FIG. 6 shows the fold change in the level of expression of the TSP-1 gene in kidney tissue obtained from subtotally (5/6) nephrectomized (SNX) rats in control and various treatment groups relative to the level of expression in kidney tissue from the control group in the study described in Example 4 (infra). Bar graph 1 shows a fold change of 1 (relative to self) in TSP-1 gene expression in kidney tissue from untreated control SNX rats that received vehicle (HEPES buffer) only. Bar graph 2 shows the fold change in gene expression in kidney tissue from SNX rats treated with 0.5 μg of active ADAMTS4 carboxy terminal polypeptide relative to control. Bar graph 3 shows the fold change in gene expression in kidney tissue from SNX rats treated with 2 μg of the ADAMTS4 polypeptide relative to control. Bar graph 4 shows the fold change in gene expression in kidney tissue from SNX rats treated with antibody to ADAMTS4 relative to control. See Example 4, for details.

Figure 7:
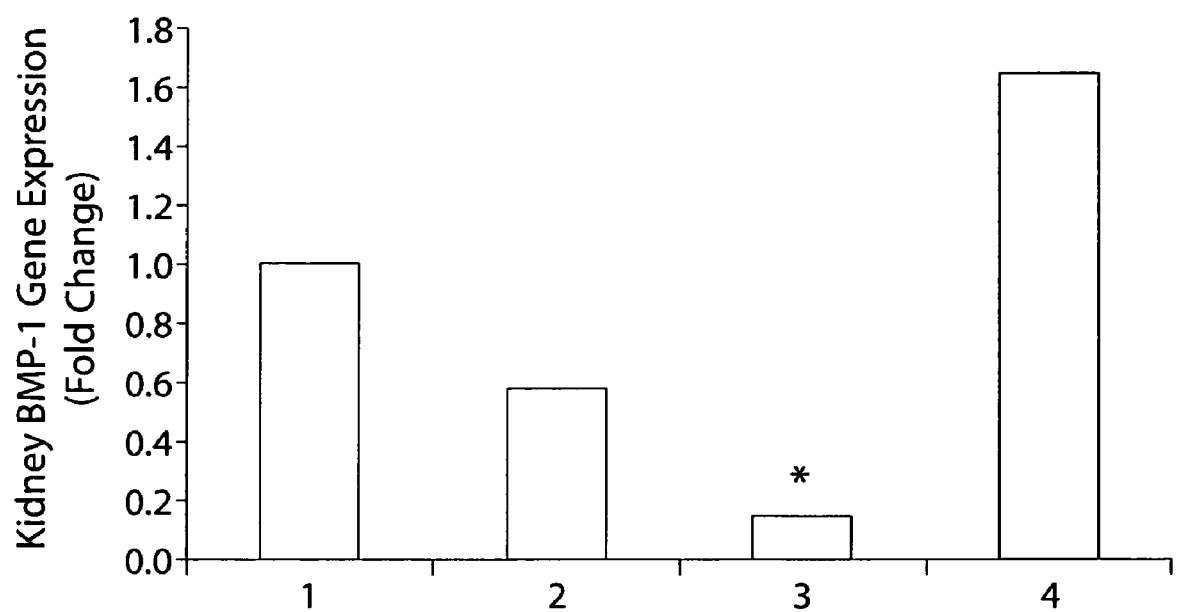

FIG. 7 shows the fold change in the level of expression of the BMP-1 gene in kidney tissue obtained from subtotally (5/6) nephrectomized (SNX) rats in control and various treatment groups relative to the level of expression in kidney tissue from the control group in the study described in Example 4 (infra). Bar graph 1 shows a fold change of 1 (relative to self) in BMP-1 gene expression in kidney tissue from untreated control SNX rats that received vehicle (HEPES buffer) only. Bar graph 2 shows the fold change in gene expression in kidney tissue from SNX rats treated with 0.5 μg of active ADAMTS4 carboxy terminal polypeptide relative to control. Bar graph 3 shows the fold change in gene expression in kidney tissue from SNX rats treated with 2 μg of the ADAMTS4 polypeptide relative to control. Asterisk indicates statistically significant decrease relative to controls (P<0.05). Bar graph 4 shows the fold change in gene expression in kidney tissue from SNX rats treated with antibody to ADAMTS4 relative to control. See Example 4, for details.

DETAILED DESCRIPTION OF THE INVENTION

The present invention is based on the discovery that that the metalloproteinase ADAMTS4 (a disintegrin and metalloproteinase with thrombospondin type 1 motif-4; also referred to as "aggrecanase-1") appears in the peripheral (venous) blood of human individuals with end-stage chronic renal failure (CRF). ADAMTS4 is not present in the blood of normal healthy human individuals. Patients in end-stage CRF have a glomerular filtration rate that is less than 10% that of normal healthy human individuals, i.e., less than 15 ml/minute/1.73 $m^2$ ("15 ml/min") and which is too low to adequately clear the blood of toxins and wastes. Accordingly, end-stage CRF patients will not survive without renal replacement therapy, such as, kidney transplantation or dialysis. As such CRF patients require dialysis to survive, they are also referred to herein as "dialysis patients".

Dialysis can temporarily clear ADAMTS4 from the circulation of a CRF patient along with other toxins and wastes that build up in the absence of adequate kidney function, but as with other toxins and wastes, ADAMTS4 gradually reappears in the blood and accumulates as a patient's condition deteriorates and time approaches for another dialysis treatment. Accordingly, ADAMTS4 is useful as a blood biomarker for end-stage CRF.

As explained more fully below, in a study using a CRF animal model, intravenous administration to CRF animals of an ADAMTS4 antibody decreased serum levels of creatinine (marker for kidney function) and prolonged survival relative to untreated control animals. These data indicate that ADAMTS4 is clearly a uremic toxin.

In addition, the data presented herein indicate that ADAMTS4 in the blood is a therapeutic target, and that administration of an ADAMTS4 inhibitor, such as a binding protein binding to ADAMTS4, e.g., an antibody to ADAMTS4, is an effective means for treating end-stage CRF to delay the need for dialysis or to extend the period of time between dialysis treatments.

In order to more clearly describe the invention the following terms are defined:

Unless indicated otherwise, when the terms "about" and "approximately" are used in combination with an amount, number, or value, then that combination describes the recited amount, number, or value alone as well as the amount, number, or value plus or minus 10% of that amount, number, or value. By way of example, the phrases "about 40%" and "approximately 40%" disclose both "40%" and "from 36% to 44%, inclusive".

The gene family referred to as "ADAM" (a disintegrin and metalloproteinase) comprises genes that share sequence similarities with the genes for snake venom metalloproteinase and disintegrin. Genes of the ADAM gene family share the original ADAM sequence motif that encodes proteins expressed on the cell surface such as fertilin, epididymal apical protein I, cyritestin, MDC, meltrin, MS2, and metargidin (see, e.g., Kuno et al., *J. Biol. Chem.*, 272(1): 556-562 (1997)). Such membrane-anchored ADAM proteins have several characteristic domains: a propeptide domain (prodomain), a metalloproteinase domain, a disintegrin domain, a cysteine-rich domain, an epidermal growth factor-like domain, a transmembrane domain, and a cytoplasmic domain.

The "ADAMTS" (a disintegrin and metalloproteinase with thrombospondin type 1 motifs (modules, or repeats)) gene family has been distinguished from the ADAM gene family. ADAMTS genes encode secreted metalloproteinases that have a domain organization that comprises a propeptide domain (prodomain), a metalloproteinase domain, a disintegrin domain, a central thrombospondin (TSP) motif, a cysteine-rich domain, a spacer domain, and a variable number of, but at least one, TSP-like motif in the carboxyl terminal region (see, e.g., Llamazares et al., *J. Biol. Chem.*, 278(15): 13382-13389 (2003)). Based on sequence differences in the metalloproteinase domain, some 60 percent of ADAM proteins (above) are actually considered to lack proteolytic activity. In contrast, the genes of the ADAMTS group encode enzymatically active metalloproteinases also known as aggrecanases. The ADAMTS family comprises at least 19 members with varied substrate preferences (see, Porter et al., *Biochem J.*, 386: 15-27 (2005)). Owing to the additional domains and aggrecanase activity of proteins encoded by ADAMTS genes, the ADAMTS genes constitute a gene family that despite some similarity in sequence arrangement is clearly distinguishable from the original ADAM gene family (see, Llamazares et al., *J. Biol. Chem.*, 278: 13382-9 (2003)).

There are at least 19 ADAMTS enzyme molecules that are involved with a variety of biological and biochemical events, including fertilization, proteoglycan degradation, processing of fibrillar collagens, intravascular coagulation, and the aggrecan degradation of articular cartilage in osteoarthritis and rheumatoid arthritis (see, e.g., Hashimoto et al., *J. Biol. Chem.*, 279(31): 32483-32491 (2004)). ADAMTS4 is synthesized as a 100 kilodalton (kDa) zymogen (p100 species). The intracellular removal of the amino (N) terminal prodomain of ADAMTS4 by furin in the trans-Golgi network to yield a 75 kDa species (p75) is necessary but not sufficient to its ability to degrade aggrecan (see, Wang et al., *J. Biol. Chem.*, 279: 15434-40 (2004)) as further processing of the carboxyl (C) terminal spacer domain must occur to yield enzymatically active 60 kDa (p60) and 50 kDa (p50) species, which differ only in the degree of C-terminal truncation (see, Hashimoto et al., *J. Biol. Chem.*, 277: 11034-11041 (2002)).

Aggrecanases have been characterized as proteinases that cleave the Glu373-Ala374 peptide bond of the aggrecan core protein. The first two aggrecanases discovered were aggrecanase-1, which is now known to be ADAMTS4 (Tortorella et al., *Science*, 284: 1664-1666 (1999)) and aggrecananse-2, which is now known to be ADAMTS5 (aggrecanase-2) (Abbaszade et al., *J. Biol. Chem.*, 274: 23443-23450 (1999)). Aggrecanases were previously described as possessing a zinc catalytic domain followed by non-catalytic ancillary domains, including a disintegrin domain, a thrombospondin domain, a cysteine-rich domain, and a spacer domain.

Some differences among the ADAMTS metalloproteinase species are noted here. For example, while the spacer domain is critical for ADAMTS4 localization in the matrix, the cysteine-rich domain influences ADAMTS5 localization (see, Gendron et al., *J. Biol. Chem.*, 282: 18294-306 (2007)). ADAMTS2, -3, and -14 have been identified as procollagen N-proteinases. ADAMTS13 maintains hemostasis through the proteolysis of von Willebrand factor following platelet binding. ADAMTS7 and ADAMTS12 have been shown to cleave cartilage oligomeric matrix protein. While ADAMTS5 is constitutively expressed in human cartilage, ADAMTS4 is inducible by a number of inflammatory cytokines, such as IL-1B, TNF-α, and TGF-β (Tortorella et al., *Osteoarthritis and Cartilage*, 9: 539-552 (2001); Yamanishi et al., *J. Immunol.*, 168: 1405-1412 (2002)). ADAMTS9 is expressed mainly in normal cartilage, whereas negligible expression of ADAMTS1, -8, and -15 has been observed in OA or normal cartilage (see, Naito et al., *Pathol. Int.*, 57: 703-711 (2007)).

Aggrecanase-mediated degradation of aggrecan, the major aggregating proteoglycan of articular cartilage, has been previously noted as an early and sustained feature of osteoarthritis (OA). In particular, in OA ADAMTS4 is highly expressed in an active form by synovial cells (synoviocytes) and chondrocytes, and, thus, is considered to play a major role in the initiation and progression of OA in human cartilage through the proteolysis of aggrecan as well as other proteoglycan and non-proteoglycan substrates predominantly at sites containing glutamate (Glu) at the P1 residue of the scissile bone (Yamanishi et al., *J. Immunol.*, 168: 1405-1412 (2002)). Gene knock out (KO) of ADAMTS5, but not of ADAMTS4, expression in mice has been shown to be chondroprotective in a surgical mouse model of OA (see, Glasson et al., *Arthritis Rheum.*, 50: 2547-2558 (2004); Glasson et al., *Nature*, 434: 644-648 (2005)), yet in human OA cartilage explants, both ADAMTS4 and ADAMTS5 mediate aggrecan breakdown (see, Song et al., *Arthritis Rheum.*, 56: 575-85 (2007)).

ADAMTS4 expression has also been found in macrophages infiltrating granulation and disc tissue during regression of lumbar disc herniation. ADAMTS proteins are also expressed in spatiotemporal patterns in follicles and cumulus oocyte complexes during ovulation relating to the broad expression pattern of versican in granulose cells and endothelial cells of the mouse ovary (see, Richards et al., *Biol. Reproduct.*, 72: 1241-1255 (2005)). In addition, there are multiple reports that show that ADAMTS proteinase are over-expressed in human cancers (see, e.g., Mochizuki et al., *Cancer Sci.*, 98: 621-628 (2007)). For example, ADAMTS4 and -5 are upregulated in proliferating glioblastoma cells, and these proteinases may contribute to the invasive potential of these cancer cells (see, Kveiborg et al., *Cancer Res.*, 65: 4754-61 (2005)).

A "binding partner" is any molecule, including any polypeptide, immunoglobulin, nucleic acid, or fragment thereof, which specifically binds a cognate binding partner (cognate ligand) at one or more sites. Examples of binding partner/cognate ligand pairs include antibody/antigen, receptor/ligand, biotin/streptavidin, and enzyme/substrate. A binding partner that is a polypeptide may also be referred to as a "binding protein". Binding partners useful in the methods and compositions described herein include binding proteins that are antibody molecules (see, below) that specifically bind ADAMTS4 or an epitope thereof. A binding partner that is a nucleic acid is referred to as an aptamer.

An "ADAMTS4-binding partner" is any binding partner molecule, including any polypeptide, immunoglobulin, nucleic acid, or fragment thereof, which binds ADMATS4 (or an epitope of ADAMATS4) at one or more sites of the binding partner molecule.

An "antibody" or "antibody molecule" includes, but is not limited to, any of the classes of full-length mammalian immunoglobulin classes (such as IgG, IgM, IgA, IgE, IgD) and subclasses thereof. An "antibody" may also be any fragment of a full-length immunoglobulin that binds the same antigen (or same epitope of an antigen). Such antibody molecules include Fab, F(ab')$_2$, and Fv fragments, as well as binding molecules that may be produced by protein engineering or recombinant DNA technology, including but not limited to, a chimeric antibody, which comprises a binding domain or complementarity determining regions (CDRs) of an immunoglobulin fused or inserted into another immunoglobulin; a humanized antibody, which comprises the CDRs from a non-human antibody inserted into the framework of a human antibody molecule; a single chain antibody (scFv); and a diabody (see, e.g., Holliger et al., *Proc. Natl. Acad. Sci. USA*, 90: 6444-6448 (1993)).

In a full-length immunoglobulin molecule (e.g., IgG), each heavy chain is comprised of a heavy chain variable region (VH) and a heavy chain constant (CH) region. The heavy chain constant region is comprised of three domains, CH1, CH2, and CH3. Each light chain is comprised of a light chain variable region or domain (VL) and a light chain constant region or domain (CL). The VH and VL regions can be further subdivided into regions of hypervariability termed "complementarity determining regions" (CDRs), interspersed with regions that are more conserved, referred to as "framework regions" (FRs). Each VH and VL comprises three CDRs and four FRs, arranged from amino terminus to carboxy terminus in the following order: FR1, CDR1, FR2, CDR2, FR3, CDR3, FR4. Full-length immunoglobulin molecules may be of any type (e.g., IgG, IgE, IgM, IgD, IgA, and IgY), class (e.g., IgG1, IgG2, IgG 3, IgG4, IgA1 and IgA2), or subclass.

An antibody useful in the methods and compositions described herein may be monovalent, i.e., having a single binding site for binding a single antigen (or epitope) molecule, or multivalent, i.e., having more than one binding site for binding more than one antigen (or epitope). A classic IgG antibody molecule has two antigen binding sites and, thus, is bivalent.

An antibody useful in the methods and compositions described herein may be monospecific, i.e., binding a single type of antigen (or epitope), or multispecific, i.e., binding two or more different antigens (or epitopes). A classic IgG antibody molecule that has two identical antigen binding sites is thus bivalent (two binding sites) and monospecific with respect to the type of antigen (or epitope) that it can bind. A bispecific antibody binding partner useful in the invention can bind at least one molecule of one antigen (or epitope thereof) and at least one molecule of another different antigen (or epitope). Bispecific antibody molecules may be heterodimers of two halves of two different full-length immunoglobulin molecules. For example, bispecific antibodies have been described using "quadroma" technology that fuses two different hybridoma cell lines, each capable of expressing a monoclonal antibody that binds a different antigen. Random pairing of light and heavy chains of the two monoclonal antibodies include heterodimers comprising a pair of heavy and light chains of one monoclonal antibody associated with a pair of heavy and light chains of the other monoclonal antibody (see, e.g., Milstein et al., *Nature*, 305: 537-540 (1983)). A variety of other bispecific antibody molecules have been described using protein engineering and recombinant DNA technology (see, e.g., Kriangkum et al., *Biomol. Eng.*, 18(2): 31-40 (2001)). Bispecific antibodies useful in the invention may include, but are not limited to, bispecific diabodies (e.g., Holliger et al. (1993); Holliger et al., *Cancer Immunol. Immunother.*, 45: 128-130 (1997); Wu et al., *Immunotech.*, 2(1): 21-36 (1996)), bispecific tandem scFv molecules, Fab mulitmers (see, e.g., Miller et al, *J. Immunol.*, 170: 4854-4861 (2003)), and dual variable domain immunoglobulins (see, e.g., Wu et al., *Nature Biotechnology*, (Oct. 14, 2007)).

Antibodies useful in the invention may be "polyclonal" antibodies, i.e., a population of different antigen-binding molecules that bind to different sites on an antigen, or "monoclonal" antibodies, i.e., a population of identical antigen-binding molecules that bind to only one site on an antigen. Polyclonal antibodies may be produced using standard methods known in the art in which an antigen is administered to an animal under conditions that elicit an immune response by the animal resulting in the production of antibodies to the antigen. Typically, such polyclonal antibodies are produced in the blood of an animal and can be isolated in the serum portion of the blood (antiserum). Further purification may provide a polyclonal antibody preparation of enhanced purity or the isolation of specific classes of antibodies from the antiserum. Monoclonal antibodies may be produced using hybridoma methods well known in the art.

A rodent hybridoma cell lines that produces a monoclonal antibody is a ready source of DNA that encodes the constant and variable regions of the expressed monoclonal antibody molecule. Especially useful is the isolation and sequence determination of DNA encoding the individual complementarity determining regions (CDRs) and framework regions (FRs). Isolated or synthesized DNA encoding the individual CDRs, FRs, and/or portions thereof, of a particular rodent monoclonal antibody can be readily employed in standard methods for producing humanized antibodies, which bind the same antigen as the rodent monoclonal antibody, but are less immunogenic when injected into humans. See, e.g., U.S. Pat. No. 5,693,762; Queen et al., *Proc. Natl. Acad. Sci. USA*, 86: 10029-10033 (1989); European Patent No. 0 239 400 B1.

Various antibody constructs have shown that antigen-binding function can be performed by fragments or portions of a full-length immunoglobulin molecule. Such antibody constructs may have bivalent-monospecific (binding two identical antigen molecules), bi- or dual specific (binding two different antigen molecules), or multi-specific formats that may bind a combination of two or more different antigens. Examples of antibody constructs encompassed within the term "antibody" include a Fab fragment, which is a monovalent fragment consisting of the VL, VH, CL, and CH1 domains; a F(ab')$_2$ fragment, a bivalent fragment comprising two Fab fragments linked by a disulfide bridge at the hinge region of an immunoglobulin molecule; an Fd fragment consisting of the VH and CH1 domains; an Fv fragment consisting of the VL and VH domains of a single arm of an antibody; a single domain antibody (dAb) (Ward et al., *Nature*, 341: 544-546 (1989); Winter et al., PCT publication WO 90/05144 A1, incorporated herein by reference), which comprises a single variable domain; dual variable domain (DVD) antibodies; and isolated complementarity determining regions (CDRs) of V regions of an antibody molecule. It is well known that Fab fragments are readily generated by digestion of a full-length antibody molecule with papain and that F(ab')$_2$ fragments can be generated by digestion of a full-length antibody molecule with pepsin.

Although the two domains of an Fv fragment, VL and VH, are coded for by separate genes, the genes encoding the domains can be joined with a synthetic linker sequence using recombinant DNA methods so that the recombinant gene encodes a single protein chain in which the VL and VH regions are joined via a peptide linker to form a monovalent molecule known as single chain Fv (scFv) (see e.g., Bird et al. *Science*, 242: 423-426 (1988); Huston et al., *Proc. Natl. Acad. Sci. USA*, 85: 5879-5883 (1988)). Such scFv antibody constructs possess a ligand (antigen, epitope thereof) binding domain and therefore are encompassed by the term "antibody" and may be used in methods and compositions described herein. As noted above, diabodies are also encompassed by the term "antibody". Diabodies are bivalent, bispecific antibodies in which VH and VL domains are expressed on a single polypeptide chain, but using a linker that is too short to allow for pairing between the two domains on the same polypeptide chain, thereby forcing the domains to pair with complementary domains of another polypeptide chain and creating two antigen binding sites (see, e.g., Holliger et al., *Proc. Natl. Acad. Sci. USA,* 90: 6444-6448 (1993); Poljak et al., *Structure,* 2: 1121-1123 (1994)).

All of the above antibody molecules are binding proteins useful in methods and compositions described herein if they comprise a functional binding domain for ADAMTS4, or an epitope thereof. Accordingly, an "ADAMTS4 antibody" is a binding protein that comprises at least one functional antigen binding site that binds ADAMTS4, or an epitope thereof.

Binding proteins useful in the methods and compositions described herein also encompass fusion proteins comprising at least one binding domain for the target ligand, e.g., ADAMTS4, linked to another polypeptide. Fusion proteins may be readily produced using standard methods including recombinant DNA methods, polymerase chain reaction (PCR), or automated protein synthesis.

A binding protein useful in methods and compositions described herein may also take the form of a fusion protein comprising a cell receptor molecule or ligand-binding portion thereof linked to an immunoglobulin (Ig) Fc region. Such fusion proteins typically possess a structure that mimics an antibody Ig molecule and, owing to the Fc region, may form dimeric or other multimeric forms in a manner similar to IgG or IgM molecules. An example of such cell receptor/Fc fusion proteins is the therapeutic drug etanercept. Etanercept is a dimeric fusion protein consisting of the extracellular ligand-binding portion of the human 75 kilodalton (p75) tumor necrosis factor receptor (TNFR) linked to the Fc portion of human IgG1. The Fc component of etanercept contains the CH2 domain, the CH3 domain, and the hinge region, but not the CH1 domain, of IgG1. As demonstrated by etanercept, such Fc fusion binding proteins may be effective as therapeutic agents for use in humans. Moreover, an additional feature of having a structure similar to that of antibody Ig molecules, Fc fusion proteins can be employed diagnostically in any of the various immunodetection assay formats available in the art (e.g., ELISA, affinity chromatography, microtiter plates, biochip technology) to detect the presence of the target ligand protein in various samples or compositions.

A composition or method described herein as "comprising" (or which "comprises") one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited, composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and close-ended composition or method "consisting of" (or which "consists of") the named elements or steps to the exclusion of any other unnamed element or step.

In any composition or method disclosed herein, known or disclosed equivalents of any named essential element or step may be substituted for that element or step.

Unless specifically indicated, a composition or method is not limited by any particular order of the listed elements or steps.

It is also understood that an element or step "selected from the group consisting of" refers to one or more of the elements or steps in the list that follows, including combinations of any two or more of the listed elements or steps.

Unless indicated otherwise, the meaning of other terms will be clear from the context or will be understood to be the same as understood and used by persons skilled in the art, including the fields of immunology, medicine, molecular biology, pharmacology, and proteomics.

ADAMTS4 is not a normal component of the circulating blood of healthy human individuals. As shown in Example 1 (infra), an analysis of protein species in blood obtained from adult human patients with chronic renal failure (CRF) on dialysis revealed for the first time the presence of ADAMTS4 in circulating blood.

Figure 1:
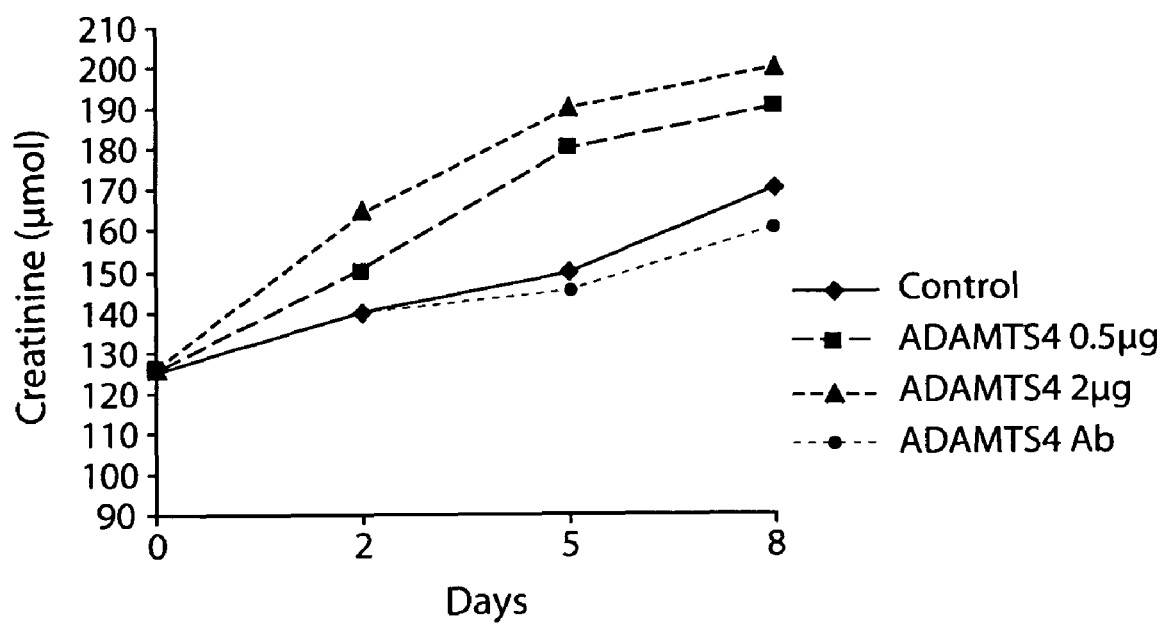
FIG. 1 is a graph of creatinine (μmol) over time (days following 5/6 nephrectomy) in blood samples obtained from subtotally (5/6) nephrectomized (SNX) rats in various groups in the study described in Example 2 (infra). Diamonds indicate untreated (vehicle only) control group of SNX rats (SNX; n=12 rats). Squares indicate group of SNX rats treated with active ADAMTS4 carboxy terminal region polypeptide (0.5 μg ADAMTS4 polypeptide per animal, 1.5 μg/kg, 2 times/week; n=12). Triangles indicate group of SNX rats treated with ADAMTS4 polypeptide (2.0 μg per animal, 6 μg/kg, 2 times/week; n=12). Circles indicate group of SNX rats treated with ADAMTS4 polyclonal antibody (#28285, Abcam Inc., Cambridge, Mass.). See Example 2, for details.

The physiological effect of the presence of ADAMTS4 in the blood is both abnormal and pathological, as ADAMTS4 is a uremic toxin whose effect can be reversed by therapeutic administration of an ADAMTS4-binding partner, such as an ADAMTS4 antibody. This was demonstrated in the study described in Example 2 (infra) of the effect of ADAMTS4 in the blood on health and survival using the 5/6 nephrectomy rat model of CRF (see, e.g., Borovecki et al, In *Bone morphogenetic proteins: Regeneration of bond and beyond* (Vukicevic and Sampath, eds.) (Birkhauser Verlag, Basel, 2004), pages 213-243). The subtotally nephrectomized (SNX) rats were divided into groups that received doses of an ADAMTS4 carboxy terminal polypeptide, which is proteolytically active; an ADAMTS4 antibody; or buffer vehicle (control group). Kidney function was monitored by following the blood and urine levels of creatinine, a standard marker for assessing kidney function. Increasing levels of creatinine in the blood indicate decreasing ability of the kidneys to filter out toxins and wastes from the blood. Intravenous administration of the ADAMTS4 polypeptide clearly increased the pathological condition of induced CRF as evidenced by significantly higher serum levels of creatinine as compared to control CRF animals and to CRF animals that were administered the antibody raised to the ADAMTS4 polypeptide. See, FIG. 1. Moreover, animals that were treated with ADAMTS4 polypeptide had a significantly higher mortality rate than control rats or rats treated with the ADAMTS4 antibody. See, FIG. 2. These findings clearly show that ADAMTS4 in the blood acts as a uremic toxin that aggravates the loss of kidney function and increases pathology and mortality of the CRF individual due to loss of adequate kidney function. Thus, the toxic effects of ADAMTS4 in the blood can be neutralized by administration of an effective amount of an ADAMTS4 antibody.

ADAMTS4 in the blood of CRF patients is a uremic toxin that can be removed by dialysis, but like other toxins and wastes that are not effectively cleared from circulation in CRF patients, ADAMTS4 will reappear and accumulate in the blood, and ultimately another dialysis treatment will be indicated. This was demonstrated in the study described in Example 3 (infra) in which blood from healthy human individuals (control group) and from CRF patients prior to and after dialysis treatment were tested for the presence of ADAMTS4 by Western immunoblotting using an antibody to ADAMTS4. The analysis revealed that an ADAMTS4 protein species of approximately 100 kilodaltons (kD) was detected by Western immunoblotting in the blood of CRF patients prior to dialysis treatment, but was not detected in the blood from healthy individuals or in the blood of the same CRF patients immediately following dialysis. Thus, dialysis can temporarily relieve a CRF patient of the toxic effects of the ADAMTS4 uremic toxin.

Since ADAMTS4 will begin to reappear and accumulate after dialysis in the blood of the CRF patient, blood levels of ADAMTS4 can be monitored to determine when an individual is in need of further dialysis treatment. An attending healthcare provider who is familiar with dialysis and CRF may monitor the level of ADAMTS4 in a patient's blood and consider it alone or in combination with other indicia of toxicity, such as serum creatinine, to determine when a patient should be administered a dialysis treatment.

As a blood biomarker of CRF and uremic toxin, a reference level or concentration range of ADAMTS4 that is indicative of need for a dialysis treatment may be obtained from a population of dialysis patients. The determination of reference levels or ranges of concentrations for blood biomarkers is the basis for virtually every biomarker currently used in diagnostic blood tests to routinely assess the health or status of organ function in human patients. Accordingly, persons skilled in the field of optimizing diagnostic blood testing for use with respect to human individuals are familiar with the procedures for use in gathering and qualifying reference levels or concentration ranges of a particular biomarker in the blood of a target population that can be routinely used by a healthcare provider to assess renal failure or to determine when there is a need to provide a dialysis treatment to a CRF patient. The same can be applied to ADAMTS4 levels to establish reference levels for a particular individual that will make monitoring of ADAMTS4 levels most meaningful and accurate as indicators of the patient's condition and need for therapy.

According to the invention, there is provided a method for detecting chronic renal failure (CRF) in a human individual comprising assaying the blood of the individual for the presence of ADAMTS4, wherein detection of ADAMTS4 in the blood (in any amount) indicates that the individual has CRF. In a preferred embodiment, an ADAMTS4 binding partner is used to detect ADAMTS4 in the blood. More preferably, an antibody to ADAMTS4 is used to detect the presence of ADAMTS4 in blood of the individual. It may be possible to detect the presence of ADAMTS4 in vivo while circulating in the periphery, e.g., using appropriate imaging systems and an ADAMTS4 binding partner, such as an ADAMTS4 antibody that is attached to an appropriate detectable label. However, in a more preferred embodiment of a method for detecting CRF in a human individual, a sample of blood is first obtained from the human individual and then assayed ex vivo for the presence of ADAMTS4 to determine if the individual has CRF.

The invention also provides a method of monitoring uremic toxicity in a dialysis patient between dialysis treatments comprising the steps of obtaining a blood sample from the patient at a first time point after a dialysis treatment, obtaining at least one additional blood sample from said patient at a later time point after the dialysis treatment, determining the level (amount, concentration) of ADAMTS4 in said first blood sample and in said at least one additional blood sample, wherein an increase in ADAMTS4 concentration between said first time point and said later time point indicates that the patient has an increasing uremic toxicity prior to said later time point. In a preferred embodiment said first time point and said later time point are within two weeks of each other. More preferably, said first time point and said later time point are within one week, even more preferably within three days, and even more preferably within two days, of each other. Alternatively, it will be advantageous to obtain blood or blood fraction samples at intervals, e.g., a week apart, more preferably three days or less apart, more preferably two days or less apart, every other day, daily, etc.

ADAMTS4 may be detected or quantitated (amount or concentration determined) in a sample of blood obtained from an individual using any of a variety of methods for assaying a sample of blood for the presence or amount of a protein of interest. For example, in a highly sensitive procedure, tryptic peptides of ADAMTS4 may be generated in a sample and then analyzed by liquid chromatography-mass spectrometry (LC-MS) (see, Example 1, below). More preferably, the presence of ADAMTS4 in a sample of blood is detected using an antibody to ADAMTS4. An antibody may be advantageously adapted to any of a variety of immunoassay formats that are available in the art for detecting or quantitating a protein of interest with a cognate antibody. Such formats include, but are not limited to, enzyme-linked immunosorbent assay (ELISA), affinity chromatography, immunoprecipitations, and biochip technology. In a typical immunoassay format, a sample of blood obtained from an individual is brought into contact with the ADAMTS4 antibody. The formation of a binding complex between an ADAMTS4 antibody and an ADAMTS4 protein present in the sample of blood is then detected using any of a variety of detection systems available in the art for detecting antibody-antigen binding complexes.

An ADAMTS4 antibody used to detect or to measure the amount of (i.e., quantitate) ADAMTS4 present in blood may be used in solution or alternatively may be immobilized on the surface of any of a variety of solid substrates. Solid substrates to which an ADAMTS4 antibody may be immobilized for use in the methods and compositions described herein include, but are not limited to, magnetic matrix particles; chromatographic matrix or resin particles (e.g., agarose); the surface of one or more wells of a plastic assay plate (such as a microtiter assay plate); pieces of a solid substrate material, such as pieces or strips of plastic, nylon, wood, paper, or other solid material, which may be dipped into or otherwise placed in contact with a blood sample or assay solution; and the surface of a silicon chip (or other chip material). Immobilization of an ADAMTS4 antibody to the surface of the wells of a microtiter plate or the surface of a chip (e.g., a silicon chip, glass slide, etc.) permits the use of formats for detecting or measuring the amount of ADAMTS4 in one or multiple blood samples using semi-automatic or fully automatic devices that are routinely used in standard high throughput ELISA or biochip assay procedures. Such devices are particularly useful for assaying large numbers of very small volumes of blood for the presence of ADAMTS4.

An ADAMTS4 antibody may be immobilized to the surface of a solid substrate by any means that preserves the ability of the antibody to bind to ADAMTS4 when brought into contact with a sample of blood that contains ADAMTS4 to form a binding complex. For example, an antibody may be immobilized to a solid substrate by adsorption (non-covalent adherence) or by covalently linking the antibody directly to the solid surface or to a linker molecule that permits the antibody to be tethered to the solid substrate.

Methods to detect a binding complex comprising ADAMTS4 and an ADAMTS4 antibody preferably employ a detection system that uses one or more signal-generating molecules (detectable labels) that will generate a signal that is easily detected by the human eye or is readily detected or measured by a signal detection instrument. Such signals useful in detecting binding complexes include, but are not limited to, a fluorescent signal, e.g., as generated from a fluorescent dye or cyanin molecule that can be attached directly or indirectly to an ADAMTS4 antibody; a visible color signal, e.g., as generated with an enzyme or colored molecule (e.g., a pigment) that can be attached directly or indirectly to an ADAMTS4 antibody; a radioactive signal, e.g., as generated by a radioisotope that can be attached directly or indirectly to an ADAMTS4 antibody; and a light signal, e.g., as generated by a chemiluminescent or bioluminescent system. An example of a bioluminescent system is a luciferin-luciferase system in which a luciferase may be attached directly or indirectly to an antibody to generate a detectable light signal in the presence of the luciferin substrate.

A detectable label may be conjugated to an ADAMTS4-binding partner, such as an ADAMTS4 antibody, directly or via a linker molecule using standard reagents and protocols available in the art. Alternatively, an ADAMTS4-binding partner may be unlabeled and a secondary binding molecule that binds either the ADAMTS4-binding partner or that binds the ADAMTS4 in the binding complex may be used to generate a detectable signal. This format is exemplified by the standard sandwich immunoassay in which a "capture antibody" (e.g., ADAMTS4 antibody) binds an antigen of interest (e.g., ADAMTS4) to form a binding complex and a secondary antibody comprising a detectable label is then provided that binds the capture antibody or the antigen of interest in the binding complex (see, e.g., detection of immune complexes on Western immunoblots in Example 3). It is understood that if the secondary antibody is also an ADAMTS4 antibody, then it must bind to a site on ADAMTS4 that is not bound by the capture antibody and that is exposed on the binding complex formed between the capture antibody and ADAMTS4. Other variations of the sandwich immunoassay are known to the skilled practitioner and adaptable for use in the methods described herein.

In another assay format, ADAMTS4 in a sample of blood is detected using an assay strip to which an ADAMTS4-binding partner, such as an ADAMTS4 antibody, is adsorbed or covalently linked. Such assay strips provide a convenient means to detect or measure ADAMTS4 in a sample of blood. For example, an assay strip containing immobilized ADAMTS4 antibody may be brought into contact with a blood sample by manually or robotically dipping the strip into the sample or dropping a sample of blood on the strip. The assay strip then may be rinsed to remove unbound material and may optionally be dipped into a blocking agent, such as bovine serum albumin or other composition, to reduce non-specific binding by potentially interfering molecules. If necessary, the assay strip may be further dipped or contacted with any reagent that is necessary to develop or generate a measurable signal that indicates the presence on the strip of a binding complex comprising ADAMTS4 bound to the immobilized ADAMTS4 antibody. The assay strip is then observed visually or read by an appropriate detection instrument to determine the presence or amount of ADAMTS4 in the sample.

A method described herein for detecting ADAMTS4 in the blood of an individual may employ whole blood or a fraction of the whole blood, such as plasma or serum. The ultimate determination of whether to use whole blood, plasma, or serum, or even some other blood fraction, in any particular assay format is well within the understanding and judgment of persons of ordinary skill in the art. Generally, plasma is preferred.

The use of standard methods and equipment for obtaining blood samples from individuals, including, without limitation, sterile needles, sterile syringes, sterile partially evacuated blood sample tubes, for obtaining blood samples from human individuals are well known by phlebotomists and healthcare providers. In addition, when a CRF patient is connected to dialysis equipment, blood samples may be conveniently obtained prior to and immediately following dialysis.

To accurately measure (quantitate) the level (amount, concentration) of ADAMTS4 in a sample of blood obtained from an individual (and, thereby, in the circulation of the individual), a standard curve may be generated graphically or computationally using an assay as described herein. For example, an assay described herein may be carried out on one or more blood samples and on a series of solutions containing known concentrations of ADAMTS4 (ADAMTS4 standards). The signal intensity or magnitude obtained for each ADAMTS4 standard is then used to construct a standard curve that correlates the signal intensity or magnitude with an amount or concentration of ADAMTS4. The signal intensity or magnitude from a sample of unknown ADAMTS4 content may then be read on the standard curve to determine the corresponding level (amount, concentration) of ADAMTS4 present in the sample. Preferably, the level of ADAMTS4 in a sample of unknown ADAMTS4 content is determined by interpolation, i.e., by reading a signal magnitude or intensity from the sample of unknown ADAMTS4 content on an area of the standard curve generated or drawn between at least two ADAMTS4 standard points. Less preferred, but optionally, the determination of the amount of ADAMTS4 in a sample may be made by extrapolation, wherein the magnitude or intensity of a signal falls on an area of the standard curve that is drawn or generated beyond or outside of two or more ADAMTS4 standard points.

Methods and compositions described herein preferably employ an ADAMTS4 antibody as the preferred ADAMTS4-binding partner to detect or quantitate ADAMTS4 in a sample of blood. Nevertheless, it is also understood that such methods and compositions may comprise the use of an ADAMTS4-binding partner other than an ADAMTS4 antibody molecule if that binding partner can be similarly employed or adapted for use in the methods and compositions.

Materials necessary for detection of ADAMTS4 in a sample of blood may be conveniently assembled into a kit that permits a healthcare provider to determine whether an individual suffers from chronic renal failure (CRF) or is in need of dialysis. In one embodiment, a kit of the invention comprises an ADAMTS4 binding partner and instructions that indicate how to use the kit to carry out the assay for ADAMTS4 in a sample of blood. In another embodiment, a kit may comprise a first binding partner, wherein the first binding partner binds ADAMTS4; a second binding partner molecule, wherein the second binding partner contains a detectable label and wherein the second binding partner is capable of binding to the first binding partner or to a site on ADAMTS4 that is not bound by the first binding partner; and instructions that indicate how to use the kit to carry out the assay to detect or quantitate ADAMTS4 in a sample of blood. The first binding partner in a kit may be used in a solution or may be immobilized on a solid substrate, such as a chip, bead, assay strip, wells of a microtiter plate, and the like, which can be brought into contact with a sample of blood. Preferably, the first binding partner is an ADAMTS4 antibody and the second binding partner is an antibody that binds either the first binding partner or to a site on ADAMTS4 that is not bound by the first binding partner. The component first and second binding partners in a kit described herein may be packaged in a variety conditions such as a dry state, an unhydrated state, a freeze-dried state, a dehydrated state, or a hydrated state in a physiological buffer solution. Solutions for hydrating, washing, blocking non-specific binding, or for signal generation from the detectable label may also be included in the kits described herein. A kit may also include one or more devices to obtain a sample of blood from a human individual. Such a device includes but is not limited to a sterile pin, a sterile needle, a sterile needle and syringe, and a sterile evacuated blood sample tube.

The presence of ADAMTS4 in the blood of individuals is not only useful as a biomarker to detect chronic renal failure (CRF), but, as shown in the study with the animal model for CRF in Example 4 (infra), is also correlated with a distinct change in the pattern of expression of certain genes in the kidney tissue of an individual with CRF. In particular, the appearance of ADAMTS4 in the blood is correlated with an increase in the level of expression in kidney tissue of the proteoglycan-4 (lubricin) and aggrecan genes and with a decrease in kidney tissue in the level of expression of the BMP-7 (bone morphogenetic protein-7), TSP-1 (thrombospondin-1), and BMP-1 (bone morphogenetic protein-1) genes. Thus, the change in expression of these genes in kidney tissue may be individually or in combination to detect CRF in an individual.

The expression of a gene may be readily detected and measured by any of a variety of standard methods, including determining the level of a gene product encoded by a gene or determining the level of RNA transcription of a gene. For example, a gene product may be detected by assaying for a known activity of the gene product (e.g., enzyme activity, binding activity) in a sample or by using an antibody to identify or measure the amount of gene product in a sample. Measuring the level of RNA transcription of a particular gene is routinely used to detect and measure gene expression. For example, the level of RNA transcription of the proteoglycan-4, aggrecan, BMP-7, TSP-1, and BMP-1 genes in samples of kidney tissue can be readily determined using a polymerase chain reaction (PCR) protocol that employs specific primer molecules to detect the specific RNA transcripts of each gene (see, Example 4, infra). Samples of kidney tissue from an individual may be readily obtained by standard renal biopsy.

Accordingly, the invention provides a method of detecting chronic renal failure (CRF) in an individual comprising the steps of obtaining a sample of kidney tissue from the individual at a first time point, obtaining at least one additional sample of kidney tissue from said individual at a later time point, determining the level of gene expression of the proteoglycan-4 gene, the aggrecan gene, the BMP-7 gene, the TSP-1 gene, the BMP-1 gene, or combination thereof, in said first kidney tissue sample and in said at least one additional kidney tissue sample, wherein the individual is determined to have CRF by a change in gene expression selected from the group consisting of an increase in the level of expression of the proteoglycan-4 gene, an increase in the level of expression the aggrecan gene, a decrease in the level of expression for the BMP-7 gene, a decrease in the level of expression of the TSP-1 gene, a decrease in the level of the BMP-1 gene, or combinations thereof. Preferably, the first time point and the later time point are within two weeks of each other. More preferably, the first time point and the later time point are within one week, even more preferably within three days, and even more preferably within two days, of each other.

ADAMTS4 in the blood of a human individual is also a therapeutic target for the treatment of chronic renal failure (CRF). The invention provides a method of treating a human individual for CRF comprising the step of administering an ADAMTS4 antibody to the individual in an amount effective to reduce or clear the presence of ADAMTS4 from the blood of the individual or to inhibit the proteinase activity of ADAMTS4. Preferably, the ADAMTS4 antibody is administered to the individual parenterally, and, more preferably, intravenously. Such treatments are expected to be ongoing, as ADAMTS4 is continuously produced in the blood of CRF patients. Accordingly, the blood of a CRF patient is routinely monitored for the reappearance of ADAMTS4 as an indication that another administration of ADAMTS4-binding protein (or some alternative or additional therapeutic treatment) is required.

The invention also provides a method of increasing the time between dialysis treatments for an individual with CRF comprising administering to the individual an ADAMTS4 antibody to reduce, inhibit, neutralize, or clear ADAMTS4 in the blood of the individual. Preferably, the ADAMTS4 antibody is administered to the individual parenterally, and more preferably, intravenously. Again, treatments are expected to be ongoing as ADAMTS4 is continuously produced in the blood of CRF patients. Accordingly, the blood of a CRF patient is routinely monitored for the reappearance of ADAMTS4 as an indication that another administration of ADAMTS4-binding protein (or some alternative or additional therapeutic treatment) is required.

It is understood that in methods described herein for treating human individuals, an ADAMTS4 antibody is prepared using methods and compositions well known in the art for the administration of a therapeutic antibody to human individuals. A composition comprising an antibody to ADAMTS4 may be formulated for administration by any of a variety routes or modes of administration. Preferably, a composition is formulated for parenteral administration, e.g., intravenous, subcutaneous, intraperitoneal, intramuscular. More preferably, a composition is formulated for intravenous. Such administration may be carried out by injection or infusion of the ADAMTS4 antibody.

Compositions comprising an ADAMTS4 antibody for administration to a human individual may comprise an effective amount of an ADAMTS4 antibody in combination with one or more pharmaceutically acceptable components such as a pharmaceutically acceptable carrier (vehicle, buffer), excipient, or other ingredient. By "pharmaceutically acceptable" is meant that a compound, component, or ingredient of a composition is compatible with the physiology of a human individual and also is not deleterious to the effective activity of the ADAMTS4 antibody component or to a desired property or activity of any other component that may be present in a composition that is to be administered to a human individual. Examples of pharmaceutically acceptable carriers include, but are not limited to, water, saline, phosphate buffered saline, dextrose, glycerol, ethanol and the like, as well as combinations thereof. In many cases, it will be preferable to include isotonic agents, including, but not limited to, sugars; polyalcohols, such as mannitol or sorbitol; sodium chloride; and combinations thereof. Pharmaceutically acceptable carriers may further comprise minor amounts of auxiliary substances such as wetting or emulsifying agents, preservatives or buffers, which enhance the shelf life or effectiveness of the antibody. An excipient is generally any compound or combination of compounds that provides a desired feature to a composition. The pH may be adjusted in a composition as necessary, e.g., to promote or maintain solubility of component ingredients, to maintain stability of one or more ingredients in the formulation, and/or to deter undesired growth of microorganisms that potentially may be introduced at some point in the procedure.

Compositions comprising an ADAMTS4 antibody may also include one or more other ingredients such as other medicinal agents (e.g., antibiotics, anti-inflammatory compounds, anti-viral agents, anti-cancer agents), fillers, formulation adjuvants, and combinations thereof.

The compositions according to the invention may be in a variety of forms. These include, but are not limited to, liquid, semi-solid, and solid dosage forms, dispersions, suspensions, tablets, pills, powders, liposomes, and suppositories. The preferred form depends on the intended route of administration. Preferred compositions are in the form of injectable or infusible solutions, such as compositions similar to those used for passive immunization of humans with other antibodies. In a preferred embodiment, an ADAMTS4 antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other structure suitable for high drug concentration. Sterile injectable solutions may be prepared by incorporating the active compound, i.e., an antibody to ADAMTS4, in the required amount in an appropriate solvent, optionally with one or a combination of ingredients that provide a beneficial feature to the composition, as required, followed by filtered sterilization. Generally, dispersions are prepared by incorporating the active ingredient into a sterile vehicle that contains a basic dispersion medium and optionally one or more other ingredients that may be required for adequate dispersion. In the case of sterile, lyophilized powders for the preparation of sterile injectable solutions, preferred methods of preparation include vacuum drying and spray-drying that produce a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

An antibody to ADAMTS4 may be administered by a variety of methods known in the art, although a preferred route/mode of administration is parenteral administration and, more preferably, intravenous administration. As will be appreciated by the skilled artisan, the route and/or mode of administration will vary depending upon the desired results. In certain embodiments, an antibody may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. A variety of methods for the preparation of such formulations are known to those skilled in the art.

Additional embodiments and features of the invention will be apparent from the following non-limiting examples.

EXAMPLES

Example 1

Identification of ADAMTS4 in Peripheral Blood of Dialysis Patients with Chronic Renal Failure (CRF)

This study identified ADAMTS4 in the peripheral blood of dialysis patients as a marker of chronic renal failure.
The following materials and methods were employed in this study.

Plasma Collection

Human blood plasma samples were supplied by the General Hospital Sveti Duh. The approval for the collection of the samples was obtained from the Ethics Committee of the same institution. Blood samples from 30 adult humans (30-70 years old, male and female) with a chronic renal failure and prescribed to undergo dialysis were drawn (before dialysis) into syringes containing 3.8% sodium citrate to form an anticoagulant-to-blood ratio of 1:9 (v/v). Plasma was obtained by centrifugation (15 min at 3000×g), and aliquots of each adult blood sample were pooled for further analysis. Aliquot samples were stored at −80° C. until analysis.

Affinity Column Purification

Pooled plasma of these chronic renal failure patients (80 ml) was diluted 2-fold with 10 mM sodium phosphate buffer (pH 7), and applied to a heparin Sepharose column (Amersham Pharmacia Biotech), previously equilibrated with 10 mM sodium phosphate buffer (pH 7). Bound proteins were eluted from the column with 10 mM sodium phosphate buffer (pH 7) containing 1 M and 2 M NaCl. Eluted fractions were precipitated with saturated ammonium sulfate (SAS) to a final concentration of 35%.

SDS Gel Electrophoresis and In-gel Digestion

SDS-PAGE was run on a NuPAGE 10% Bis-Tris gel (Invitrogen, Carlsbad, USA) using MOPS SDS buffer system, and subsequently stained with Coomassie staining kit (NuPAGE, Invitrogen), as instructed by the manufacturer. After staining, each of the 15 gel lanes was sliced from the gel. The pieces were then subjected to in-gel reduction, alkylation, and trypsin digestion as described previously [4]. Gel pieces were washed two times with acetonitrile/25 mM $NH_4HCO_3$, reduced by incubation with 10 mM dithiothreitol (DTT) for 45 minutes at 56° C., and carboxyamidomethylated by incubation in 55 mM iodoacetamide for 45 minutes at room temperature. Trypsin (Promega) was added to dried gel pieces (150 ng per piece, diluted in 25 mM $NH_4HCO_3$), and incubated overnight at 37° C. Tryptic peptides were extracted with formic acid/acetonitrile/$H_2O$ (10:20:70); and 100% acetonitrile, dried, and resuspended in trifluoroacetic acid/acetonitrile/$H_2O$ (1:2:97) for MS analysis.

Mass Spectrometry

Tryptic peptides were analyzed by liquid chromatography-mass spectrometry (LC-MS). An Agilent 1100 nanoflow HPLC system (Agilent Technologies) was coupled to an LTQ-Orbitrap mass spectrometer (Thermo Scientific) using a nano-electrospray LC-MS interface (Proxeon Biosystems). Peptides were loaded on a home-made 75 μm $C_{18}$ HPLC column in solvent "A" (0.5% acetic acid in Milli-Q water) and eluted with a 70-minute segmented linear gradient of 10-60% solvent "B" (80% acetonitrile, 0.5% acetic acid in Milli-Q water) at a flow rate of ca. 250 mL/min.

The mass spectrometer was operated in the positive ion mode. Each measurement cycle consisted of a full MS scan acquired in the orbitrap analyzer at a resolution of 60000, and MS/MS fragmentation of the five most-intense ions in the linear ion trap analyzer. To further improve mass accuracy, the lock-mass option was used as described previously [9]. This has resulted in a typical peptide average absolute mass accuracy of less than 1 ppm.

Peak lists were generated using in-house developed software (Raw2 msm) [9], and searched against concatenated forward and reverse ("decoy") IPI human database (version 3.13) using Mascot search engine (Matrix Science). Searches were done with trypsin specificity (2 missed cleavages allowed), carboxyamidomethylation as fixed modification, and oxidized methionine as variable modification. Precursor ion and fragment ion mass tolerances were 10 ppm and 0.5

Da, respectively. Results of the database search were validated using the MSQuant software (available at hypertext transfer protocol address msquant period sourceforge period net) for quantitative proteomics/mass spectrometry.

Only peptides with a mass deviation lower than 5 ppm were accepted; two peptides were required for protein identification.

Gene ontology (GO) analysis was performed using ProteinCenter software package (Proxeon Biosystems).

Results

Identification of ADAMTS-4 as Potential Uremic Toxin

From a list of detected proteins in samples of peripheral blood obtained from patients prior to dialysis, several proteins were singled out which could be related to chronic renal failure, uremia related disorders, and/or renal failure-related effects on bone and cartilage metabolism. Among these was detected ADAMTS-4 (a disintegrin and metalloproteinase with thrombospondin type 1 motif-4, also known as aggrecanase-1). ADAMTS4 had not previously been identified in plasma of normal individuals or disease patients.

The ADAMTS4 protein was identified in plasma of patients prior to dialysis indicating that it accumulated between dialysis treatments and could have had deleterious catabolic effects on various organs prior to the next dialysis procedure. Moreover, a form of the ADAMTS4 protein was identified at several molecular weight bands with an average, statistically significant, Mascot score of 59.

The proteins of a pre-dialysis plasma proteome were identified in individual gel bands from the entire range of molecular weights following SDS-PAGE electrophoresis as described above. In comparison with the plasma from normal individuals, there were several proteins which were present only in the plasma of patients prior to dialysis. These protein species were considered as candidates as diagnostic components of a plasma proteome fingerprint for dialysis-requiring chronic renal failure. In particular, the results indicated that a candidate protein that may be used in a diagnostic proteome of dialysis-requiring (pre-dialysis) chronic kidney disease and chronic renal failure is ADAMTS4.

Example 2

A Study of ADAMTS4 in a Rat Model of Chronic Renal Failure (CRF)

The following study examined the effect of ADAMTS4 on health and survival of individuals in a rat model of chronic renal failure (CRF) (see, Borovecki et al., In Vukicevic and Sampath, eds., *Bone Morphogenetic Proteins: Regeneration of Bone and Beyond*, ((Birkhauser Verlag, Basel, 2004), pages 213-243.

Animals

Female Sprague-Dawley rats (Harlan Winkelmann, Borchen, Germany) weighing about 250 grams-300 grams were used and allowed free access to water and food.

5/6 Nephrectomy Model of CRF

Female Sprague-Dawley rats (Harlan Winkelmann, Borchen, Germany) weighing approximately 250 g-300 g were fed standard rat chow ad libitum and were given free access to water. A total of 60 animals underwent 5/6 nephrectomy (remnant kidney model). Animals were subjected to unilateral 2/3 nephrectomy (left kidney) under ketamin/diazepam anesthesia (100 mg/kg or 2.5 µg/kg, respectively). Two weeks later, the right kidney was surgically removed under anesthesia to induce chronic renal failure. Buprenorphine (0.05 mg/kg of body weight, s.c.) was used as post-operative analgesia as previously described. Subtotally nephrectomized (SNX) rats were randomly assigned into four groups of twelve animals: (1) SNX control (n=12); (2) SNX+ADAMTS4 carboxy terminal polypeptide (ab41235, Abcam Inc., Cambridge, Mass.) (0.5 µg of ADAMTS4 polypeptide per animal, 1.5 µg/kg, 2 times/week; n=12); (3) SNX+ADAMTS4 carboxy terminal polypeptide (2 µg per animal, 6 µg/kg, 2 times/week; n=12); and (4) SNX+ADAMTS4 antibody to ADAMTS4 polypeptide (ab28285, Abcam Inc., Cambridge, Mass.) (1 µg of antibody per animal, 1 µg/kg, 2 times/week; n=12). Control animals received only 30 mM HEPES buffer as a vehicle. Animals were euthanized 8 weeks following SNX by overdose of sodium pentobarbital.

Blood samples and 24-hour urine collections from animals in metabolic cages were taken each week from week 1 to 8. Serum and urine creatinine was measured with the standard Jaffé method. The glomerular filtration rate (GFR) was determined using serum creatinine over urine creatinine as adjusted to body weights. The cumulative survival rate was also observed and recorded for both control and experimental rats.

Histology

At termination, through a combined midline laparotomy and thoracotomy, the vascular tree was exposed and the large vessels were removed en bloc. The proximal half of thoracic aorta was fixed in neutral buffered formalin for histology; the distal part was used for determination of tissue calcium content. Before embedding in paraffin, formalin-fixed aortic tissue was sectioned perpendicular to its length axis into 2 mm to 3 mm long segments (6 to 10 per animal). All aortic segments from one animal were embedded upright in the same paraffin block. Four-micrometer sections were stained with Von Kossa's method to visualize calcium containing precipitates and counterstained with hematoxylin and eosin. Vascular calcification was assessed by an observer blinded to the identity of the sections. The degree of Von Kossa positivity was scored semiquantitatively with scores ranging from 0 to 3. Score 0 indicated no Von Kossa positivity; score 1: focal Von Kossa positivity, larger than or not overlying a cell nucleus; score 2: partially circumferential Von Kossa positivity in the tunica media of the vessel; and score 3: Von Kossa positivity in the tunica media spanning the complete circumference of the vessel.

Results

Serum creatinine (Cr) concentrations increased in SNX animals throughout the duration of the experiment. See, FIG. 1. In contrast, animals that received the ADAMTS4 polypeptide at 0.5 µg per animal, two times a week, had higher Cr values at 2 to 8 weeks as compared to SNX control rats. Animals that received ADAMTS4 at 2 µg per animal, two times a week, had higher serum Cr values at 2 to 8 weeks following the beginning of treatment as compared to SNX rats. See, FIG. 1. Animals that received the ADAMTS4 antibody at 1 µg per animal, two times a week, had lower serum Cr values as compared to SNX control rats.

Figure 2:
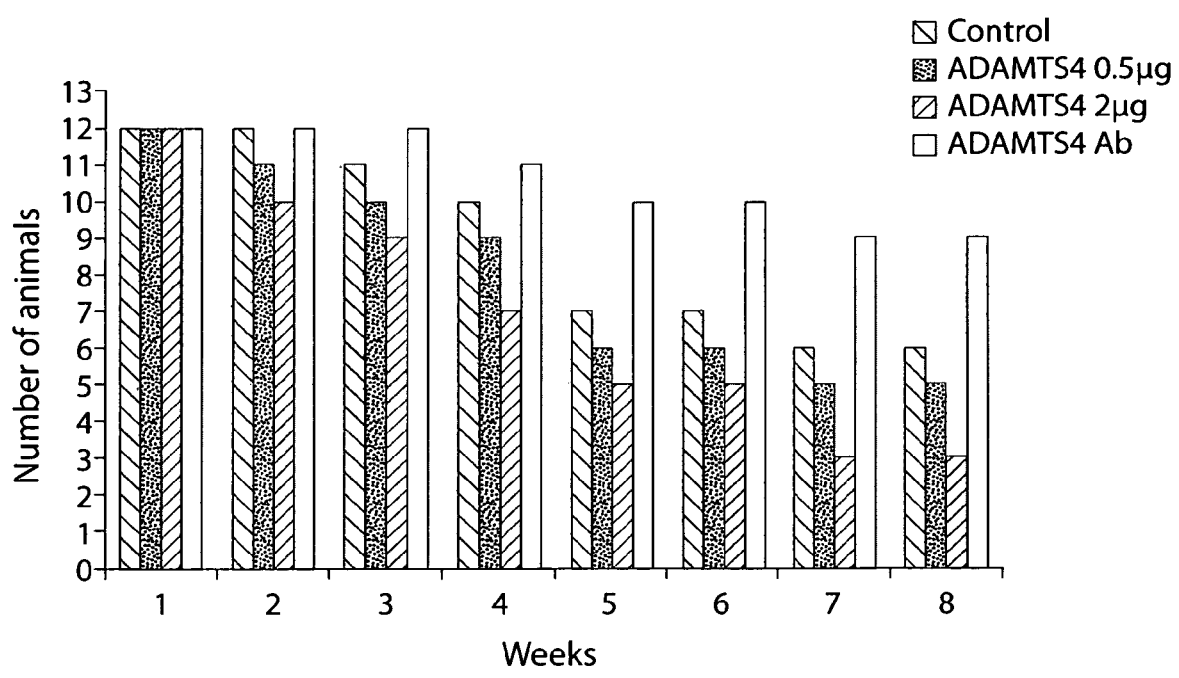
FIG. 2 shows bar graphs of the survival of subtotally (5/6) nephrectomized (SNX) rats over time (weeks) from control and treatment groups (n=12 per group) as described above in FIG. 1 for the study described in Example 2 (infra). "Control" indicates animals of untreated (vehicle only) control group. "ADAMTS4 0.5 μg" indicates animals treated with 0.5 μg of active ADAMTS4 polypeptide. "ADAMTS4 2.0 μg" indicates animal treated with 2.0 μg of active ADAMTS4 polypeptide. "ADAMTS4 Ab" indicates animals treated with ADAMTS4 polyclonal antibody. See, Example 2 for details.

As shown in FIG. 2, animals that received ADAMTS4 protein at 2 µg per animal had significantly higher mortality rate as compared to animals from the SNX control group. The survival rate of animals that received ADAMTS4 antibody was significantly increased compared to SNX control rats or rats treated with the ADAMTS4 polypeptide. See, FIG. 2.

Von Kossa staining demonstrated the calcification of blood vessels in SNX control rats, which were evaluated at week 8 to have a Von Kossa score of 2. In contrast, extensive and widespread calcified lesions were stained throughout the aorta of animals treated with ADAMTS4 (0.5 and 2 µg per animal, two times a week). Such ADAMTS4-treated animals were evaluated at week 8 to have a Von Kossa score of 3.

Interestingly, animals treated with the ADAMTS-4 antibody had a significantly lower calcification rate with a Von Kossa score of 1.

The results of this study using the 5/6 nephrectomy animal model for chronic renal failure (CRF) show that a desirable therapeutic benefit can be achieved by administering an ADAMTS4-specific binding protein, such as an anti-AD-AMTS4 antibody, to the peripheral circulation of CRF individuals. Accordingly, ADAMTS4 is a therapeutic target for treating CRF, and treatment directed against ADAMTS4 is effective when administered parenterally to the peripheral circulation.

Example 3

Detection of ADAMTS4 in Plasma from Healthy Individuals and Kidney Dialysis Patients This study examined plasma from healthy individuals and dialysis patients for the presence of ADAMTS4.

Plasma Collection

Human blood plasma samples were supplied by the General Hospital Sveti Duh. The approval for the collection of the samples was obtained from the Ethics Committee of the same institution. Blood samples were collected from 30 adult humans, 30 to 70 years old, male and female, healthy persons and those with chronic renal failure (CRF) on dialysis. In the case of the patients with chronic failure, blood samples were drawn before and after dialysis. The blood samples were drawn into syringes containing 3.8% sodium citrate to form an anticoagulant-to-blood ratio of 1:9 (v/v). Plasma was obtained by centrifugation (15 min at 3000×g), and aliquots of each adult blood sample were pooled for further analysis. Aliquot samples were stored at −80° C. until analysis.

Affinity Column Purification

Plasma samples from each group (healthy persons, CRF patients before dialysis, CRF patient after dialysis) were pooled (80 ml), diluted 2-fold with 10 mM sodium phosphate buffer (pH 7), and then applied to a heparin Sepharose column (Amersham Pharmacia Biotech) previously equilibrated with 10 mM sodium phosphate buffer (pH 7). Bound proteins were eluted from the column with 10 mM sodium phosphate buffer (pH 7) containing 1 M and 2 M NaCl. Eluted fractions were precipitated with saturated ammonium sulfate (SAS) to a final concentration of 35%.

Gel Electrophoresis and Western Immunoblot

Ammonium sulfate precipitated proteins (see, above) were resuspended in sample loading buffer and heated at 99° C. for 3 minutes for SDS-polyacrylamide gel electrophoresis (SDS-PAGE) and Western immunoblot analysis. The samples were centrifuged briefly to remove undissolved material, and the supernatants were run on SDS-PAGE (10% polyacrylamide gel, Invitrogen) in a Novex mini-gel system. After electrophoresis, proteins were transferred by electroblotting to a nitrocellulose membrane. The electroblotted nitrocellulose membrane was then incubated with the rabbit polyclonal anti-ADAMTS4 antibody. Bound anti-ADAMTS4 antibody was then detected with an alkaline phosphatase-conjugated anti-rabbit IgG immunoglobulin (Immunodetection Kit, Invitrogen).

Results

Western blot analysis using the ADAMTS4-specific antibody showed that plasma samples from CRF patients prior to dialysis contained a specific band of approximately 100 kilodalton (kD) molecular weight. The same band was not present in the plasma samples of healthy individuals. Following dialysis, the same band corresponding to ADAMTS4 was not detected in immunoblots of plasma from the CRF patients.

These data indicate that between dialysis treatments, the ADAMTS4 metalloproteinase reappears and its concentration increases in the blood of the CRF patient, reaching a peak just before the next dialysis procedure. Accordingly, in the absence of therapeutic intervention, the blood of a CRF patient on dialysis is at best only transiently cleared of this potentially catastrophic metalloproteinase that can significantly accelerate the overall decline in the health and life expectancy of the dialysis patient as the result of progressive loss of function not only of the kidneys, but eventually other tissues or organs including, but not limited to, muscle, bone, liver, heart, and brain.

The results clearly show that ADAMTS4 is a new and useful blood biomarker for diagnosing CRF in a human individual and that ADAMTS4 in the blood can be readily detected using an ADAMTS4-binding protein, such as an anti-ADAMTS4 antibody, in a standard immunodetection assay format (e.g., Western blot). Moreover, the results taken together with those in Examples 1 and 2, above, demonstrate that any therapy to inhibit ADAMTS4 activity in the circulation or to clear ADAMTS4 from the periphery must be ongoing as ADAMTS4 is continuously expressed in the blood of CRF patients.

Example 4

Effect of ADAMTS4 on Gene Expression in Kidneys of Animals with Chronic Renal Failure This study examined the effect of ADAMTS4 or an anti-ADAMTS4 neutralizing antibody on the expression of genes encoding proteoglycan-4 (lubricin), TSP-1, BMP-7, and BMP-1 in kidney tissues of animals in the 5/6 nephrectomy model for chronic renal failure (CRF).

Animals

Female Sprague-Dawley rats (Harlan Winkelmann, Borchen, Germany) weighing about 250-300 g were used and allowed free access to water and food.

5/6 Nephrectomy Model of CRF

Female Sprague-Dawley rats (Harlan Winkelmann, Borchen, Germany) weighing approximately 250-300 g were fed standard rat chow ad libitum and were given free access to water. A total of 60 animals underwent 5/6 nephrectomy (remnant kidney model). Animals were subjected to unilateral 2/3 nephrectomy (left kidney) under ketamin/diazepam anesthesia (100 mg/kg or 2.5 µg/kg, respectively). Two weeks later, the right kidney was surgically removed under anesthesia. Buprenorphine (0.05 mg/kg of body weight, subcutaneous (s.c.)) was used as post-operative analgesia. Subtotally nephrectomized (SNX) rats were randomly assigned into four groups of twelve animals: (1) SNX-control (n=12); (2) SNX+ ADAMTS-4 peptide (#41235) (0.5 µg per animal, 1.6 µg/kg, 2×/week, n=12); (3) SNX+ADAMTS-4 peptide (#41235) (2 µg per animal, 6 µg/kg, 2×/week, n=12); and (4) SNX+AD-AMTS-4 antibody (#28285ab) (1 µg per animal, 1 µg/kg, 2×/week, n=12). Control animals received vehicle only (30 mM HEPES buffer). Animals were euthanized 8 weeks following SNX by overdose of sodium pentobarbital.

Renal Function in 5/6 Nephrectomy Model of CRF

Blood samples and 24-hour urine collections from animals in metabolic cages were taken each week from week 1 to 8. Serum and urine creatinine was measured with the standard Jaffé method. The glomerular filtration rate (GFR) was determined using serum creatinine over urine creatinine as adjusted to body weights. The cumulative survival rate was also observed and recorded for both control and experimental rats.

PCR Analysis of Gene Expression

The level of expression of a gene of interest in kidney tissue was determined by measuring the level of RNA transcription of the gene. RNA was extracted using RNeasy®Mini Kit for RNA isolation (Qiagen GmbH, Hilden, Germany) according to manufacturer's protocol. All samples were treated with DNase (RNase-Free DNase Set, Qiagen GmbH). Total RNA quality and quantity was checked by spectrometry (BioPhotometer, Eppendorf). One µg of purified total RNA from kidney tissue samples were reverse transcribed with SuperScript™ III First-Strand Synthesis SuperMix RT reverse transcriptase (Invitrogen, Carlsbad, Calif.) using random hexamer primers according to the manufacturer's protocol. Expression of genes of interest was measured using a LIGHTCYCLER® FastStart DNA Master SYBR Green gene expression kit (Roche Diagnostics) in the LIGHTCYCLER® real time PCR detection instrument (Roche Diagnostics Corp., Indianapolis, Ind.). The comparative CT method (? ? CT) was used for relative quantification of gene expression and data were transformed to absolute values using 2-? ? CT formula.

Expression of three housekeeping genes (albumin, glyceraldehyde-3-phosphate dehydrogenase (GAPDH) and beta-actin) was analyzed, and geNorm version 3.5 software was used to determine the GAPDH gene was the most stably expressed. The stable level of expression of the GAPDH gene (RNA transcription) was therefore used as an internal standard against which the level of expression (RNA transcription) of each gene of interest was normalized. The normalized level of expression of a particular gene in kidney tissue from animals of each of the three treatment groups was then compared with the normalized level of expression of that gene in kidney tissue from vehicle-treated (control) group to determine the fold-change in gene expression between treatment and control groups.

For proteoglycan-4 (lubricin) gene expression, primers having the following nucleotide sequences (5' to 3') were employed:

```
forward:
CCT CCT GAC CCT CCT ACT CC      (SEQ ID NO: 1)

reverse:
TGT TCT CTG CAC TCC GTG TC.     (SEQ ID NO: 2)
```

For aggrecan gene expression, primers having the following nucleotide sequences were employed:

```
forward:
CCT GCT ACT TCA TCG ACC CC      (SEQ ID NO: 3)

reverse:
AGA TGC TGT TGA CTC GAA CCT.    (SEQ ID NO: 4)
```

For TSP-1 gene expression, primers having the following nucleotide sequences were employed:

```
forward:
GAC ACA CGA CTG CAA CAA GAA     (SEQ ID NO: 5)

reverse:
GTC TCC CAC ATC ATC TCT GTC A.  (SEQ ID NO: 6)
```

For BMP-7 gene expression, primers having the following nucleotide sequences were employed:

```
forward:
ACG GAC AGG GCT TCT CCT AC      (SEQ ID NO: 7)

reverse:
ATG GTG GTA TCG AGG GTG GAA.    (SEQ ID NO: 8)
```

For BMP-1 gene expression, primers having the following nucleotide sequences were employed:

```
forward:
CCC TGA GTA TCC CAA TGG CTA     (SEQ ID NO: 9)

reverse:
CCA CAT AGT CAT ACC AGC ACA G.  (SEQ ID NO: 10)
```

Results

The effects of ADAMTS4 or an anti-ADAMTS4 neutralizing antibody on expression of BMP-7, proteoglycan-4 (lubricin), TSP-1, and BMP-1 genes in kidney tissue of 5/6 SNX rats (CRF animals) are shown in FIGS. 3-7.

Figure 3:
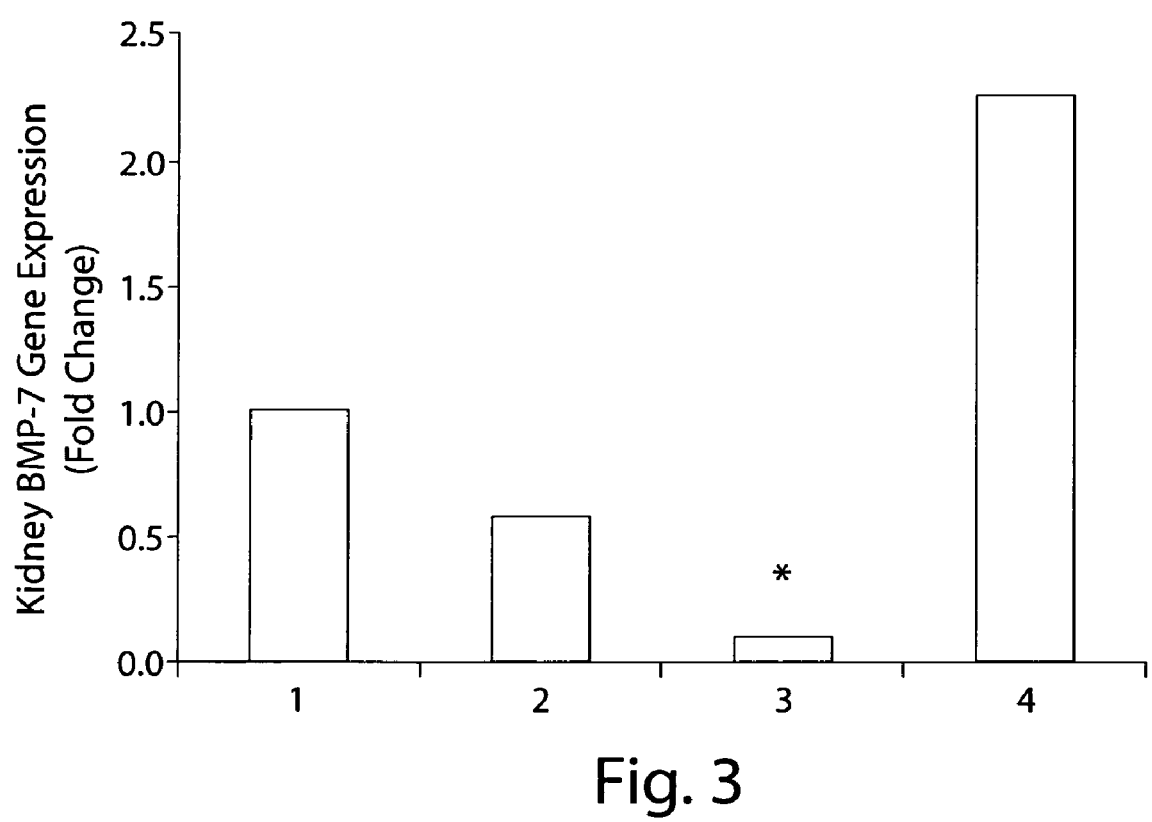
FIG. 3 shows the fold change in the level of expression of the BMP-7 gene in kidney tissue obtained from subtotally (5/6) nephrectomized (SNX) rats in control and various treatment groups relative to the level of expression in kidney tissue from the control group in the study described in Example 4 (infra). Bar graph 1 shows a fold change of 1 (relative to self) in BMP-7 gene expression in kidney tissue from untreated control SNX rats that received vehicle (HEPES buffer) only. Bar graph 2 shows the fold change in gene expression in kidney tissue from SNX rats treated with 0.5 μg of active ADAMTS4 carboxy terminal polypeptide relative to control.

As shown in FIG. 3, systemic administration of ADAMTS4 to 5/6 SNX rats (CRF animals) downregulated the expression of BMP-7, which has been shown to induce kidney regeneration in rat models of acute and chronic kidney failure (Vukicevic et al., *J. Clin. Invest.*, 102: 202-214 (1998); Borovecki et al., In Vukicevic and Sampath, eds., *Bone Morphogenetic Proteins: From Laboratory to Clinical Practice*, (Birkhauser Verlag, Basel, 2002), pages 263-288; Borovecki et al., In Vukicevic and Sampath, eds., *Bone Morphogenetic Proteins: Regeneration of Bone and Beyond*, (Birkhauser Verlag, Basel, 2004), pages 213-243).

Injection of 2 µg ADAMTS4 had a pronounced stimulatory effect on proteoglycan-4 (lubricin) gene expression (FIG. 4) as well as on aggrecan gene expression (FIG. 5). Lubricin is produced primary by human synovial fibroblasts, and is also known as MSF (megakariocyte stimulating factor). Aggrecan is a large aggregating protein, which consists of chondroitin and keratan sulphate. Lubricin and aggrecan are involved with matrix formation and cell adhesion in articular cartilage and also in the modulation of cytokine activity and in direct cell signaling. However, accumulation of such matrix in the injured kidney promotes a position of interstitial matrix which in turn eventually decreases the cellular kidney compartment.

Although not statistically significant in this study, TSP-1 gene expression showed a downward trend in CRF animals treated with ADAMTS4. See, FIG. 6. In contrast, treatment of CRF animals with ADAMTS4 neutralizing antibody upregulated the TSP-1 gene expression. An increase in TSP-1 normally precedes the undesired development of tubulointerstitial fibrosis.

As shown in FIG. 7, treatment of CRF animals with ADAMTS4 also downregulated BMP-1 gene expression, which might also be a consequence of suppression of BMP-7 expression. Treatment of CRF animals with ADAMTS4 neutralizing antibody upregulated the BMP-1 gene expression.

The results indicate that the changes in the levels of expression of the five genes in kidney tissue of an individual are correlated with, and therefore indicative of, chronic renal failure in the individual.

All patents, applications, and publications cited in the above text are incorporated herein by reference.

Other variations and embodiments of the invention described herein will now be apparent to those of ordinary skill in the art without departing from the scope of the invention.

What is claimed is:

1. A method of treating chronic renal failure in a human individual in need of treatment thereof comprising the step of:

administering to the individual an antibody to human ADAMTS4;

wherein said antibody is administered in an amount effective to reduce the level of ADAMTS4 in the blood.

2. The method according to claim 1, wherein the antibody to ADAMTS4 is administered parenterally.

3. The method according to claim 2, wherein the antibody to ADAMTS4 is administered intravenously.

4. The method according to claim 1, wherein said individual in need of treatment for chronic renal failure is a dialysis patient.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: forward primer for proteoglycan-4

<400> SEQUENCE: 1
cctcctgacc ctcctactcc                                               20

<210> SEQ ID NO 2
<211> LENGTH: 20
<212> TYPE: DNA
<213> ORGANISM: Artificial Sequence
<220> FEATURE:
<223> OTHER INFORMATION: reverse primer for proteoglycan-4

<400> SEQUENCE: 2
tgttctctgc actccgtgtc                                               20

<210> SEQ ID NO 3
<211> LENGTH: 20
<212> TYPE: DNA
<213> ORGANISM: Artificial Sequence
<220> FEATURE:
<223> OTHER INFORMATION: forward primer for m aggrecan

<400> SEQUENCE: 3
cctgctactt catcgacccc                                               20

<210> SEQ ID NO 4
<211> LENGTH: 21
<212> TYPE: DNA
<213> ORGANISM: Artificial Sequence
<220> FEATURE:
<223> OTHER INFORMATION: reverse primer for m aggrecan

<400> SEQUENCE: 4
agatgctgtt gactcgaacc t                                             21

<210> SEQ ID NO 5
<211> LENGTH: 21
<212> TYPE: DNA
<213> ORGANISM: Artificial Sequence
<220> FEATURE:
<223> OTHER INFORMATION: forward primer for TSP-1

<400> SEQUENCE: 5
gacacacgac tgcaacaaga a                                             21

<210> SEQ ID NO 6
<211> LENGTH: 22
<212> TYPE: DNA
<213> ORGANISM: Artificial Sequence
<220> FEATURE:
<223> OTHER INFORMATION: reverse primer for TSP-1

<400> SEQUENCE: 6
gtctcccaca tcatctctgt ca                                            22

<210> SEQ ID NO 7
<211> LENGTH: 20
<212> TYPE: DNA

```
<213> ORGANISM: Artificial Sequence
<220> FEATURE:
<223> OTHER INFORMATION: forward primer for BMP-7

<400> SEQUENCE: 7
acggacaggg cttctcctac                                           20

<210> SEQ ID NO 8
<211> LENGTH: 21
<212> TYPE: DNA
<213> ORGANISM: Artificial Sequence
<220> FEATURE:
<223> OTHER INFORMATION: reverse primer for BMP-7

<400> SEQUENCE: 8
atggtggtat cgagggtgga a                                         21

<210> SEQ ID NO 9
<211> LENGTH: 21
<212> TYPE: DNA
<213> ORGANISM: Artificial Sequence
<220> FEATURE:
<223> OTHER INFORMATION: forward primer for BMP-1

<400> SEQUENCE: 9
ccctgagtat cccaatggct a                                         21

<210> SEQ ID NO 10
<211> LENGTH: 22
<212> TYPE: DNA
<213> ORGANISM: Artificial Sequence
<220> FEATURE:
<223> OTHER INFORMATION: reverse primer for BMP-1

<400> SEQUENCE: 10
ccacatagtc ataccagcac ag                                        22
```